United States Patent
Umetsu et al.

(10) Patent No.: US 10,001,451 B2
(45) Date of Patent: Jun. 19, 2018

(54) CELL DETERMINATION DEVICE, CELL DETERMINATION SYSTEM, AND CELL DETERMINATION METHOD

(71) Applicant: Sony Corporation, Tokyo (JP)

(72) Inventors: Tomoyuki Umetsu, Tokyo (JP); Seungmin Lee, Tokyo (JP); Marcaurele Brun, Tokyo (JP); Yoichi Katsumoto, Tokyo (JP)

(73) Assignee: Sony Corporation, Tokyo (JP)

( * ) Notice: Subject to any disclaimer, the term of this patent is extended or adjusted under 35 U.S.C. 154(b) by 121 days.

(21) Appl. No.: 14/423,371

(22) PCT Filed: Jul. 12, 2013

(86) PCT No.: PCT/JP2013/069714
§ 371 (c)(1),
(2) Date: Feb. 23, 2015

(87) PCT Pub. No.: WO2014/038298
PCT Pub. Date: Mar. 13, 2014

(65) Prior Publication Data
US 2015/0212028 A1    Jul. 30, 2015

(30) Foreign Application Priority Data

Sep. 4, 2012  (JP) ................................ 2012-194362
Mar. 29, 2013 (JP) ................................ 2013-070851

(51) Int. Cl.
*G01N 27/02*   (2006.01)
*G01N 33/487*  (2006.01)
(Continued)

(52) U.S. Cl.
CPC ........... *G01N 27/026* (2013.01); *G01N 15/12* (2013.01); *G01N 33/48728* (2013.01); *G01N 2015/1006* (2013.01); *G01N 2015/1081* (2013.01)

(58) Field of Classification Search
CPC ................. G01N 27/026; G01N 15/12; G01N 33/48728; G01N 2015/1081; G01N 2015/1006
See application file for complete search history.

(56) References Cited

U.S. PATENT DOCUMENTS

2006/0166366 A1    7/2006   Matsumoto et al.
2010/0136606 A1    6/2010   Katsumoto et al.
(Continued)

FOREIGN PATENT DOCUMENTS

JP   2006-226996 A   8/2006
JP   2009-042141 A   2/2009
(Continued)

OTHER PUBLICATIONS

K. Cheung, et al. "Impedance Spectroscopy Flow Cytometry: On-Chip Label-Free Cell Differentiation," Cytometry, Part A, vol. 65A, 2005, p. 124-132.*

(Continued)

*Primary Examiner* — J. Christopher Ball
(74) *Attorney, Agent, or Firm* — Chip Law Group

(57) ABSTRACT

Provided is a cell determination device including a classification unit configured to classify individual cells based on one of a relaxation strength, a relaxation frequency, and low-frequency conductance obtained from a complex dielectric constant spectrum of the cells.

15 Claims, 22 Drawing Sheets

(51) Int. Cl.
*G01N 15/12* (2006.01)
*G01N 15/10* (2006.01)

(56) References Cited

U.S. PATENT DOCUMENTS

| | | |
|---|---|---|
| 2010/0228491 A1 | 9/2010 | Gutierrez et al. |
| 2011/0269221 A1 | 11/2011 | Katsumoto et al. |
| 2012/0103817 A1 | 5/2012 | Omori et al. |

FOREIGN PATENT DOCUMENTS

| | | |
|---|---|---|
| JP | 2010-181399 A | 8/2010 |
| JP | 2011-112497 A | 6/2011 |
| JP | 2012-098063 A | 5/2012 |
| JP | 2012-519848 A | 8/2012 |

OTHER PUBLICATIONS

Hoffman & Britt "Flow-System Measurement of Cell Impedance Properties", Journal of Histochemistry and Cytochemistry, vol. 27, No. 1, 1979, p. 234-240.*

S. Grimnes et al. "Chapter 3: Dielectrics" Bioimpedance and Bioelectricity Basics, 2nd Edition, London:Elsevier, 2008, p. 57-92, Google Books web, accessed Jul. 18, 2017.*

Asami et al., Dielectric analysis of mitochondria isolated from rat liver. I. Swollen mitoplasts as simulated by a single-shell model. Biochim Biophys Acta. Dec. 19, 1984;778(3):559-69.

* cited by examiner

FIG. 3
A
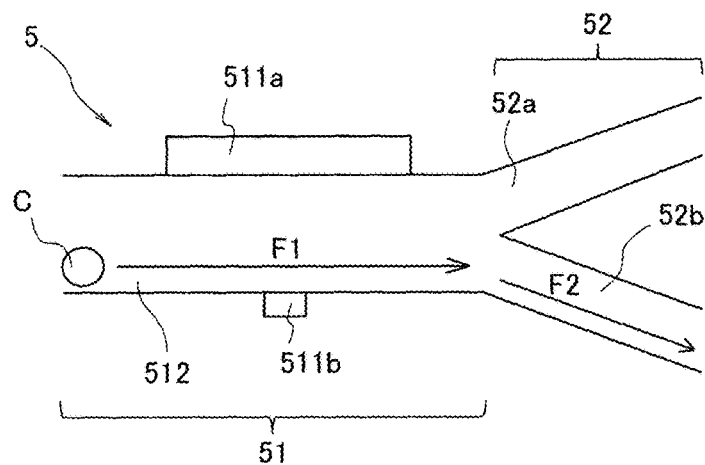
B
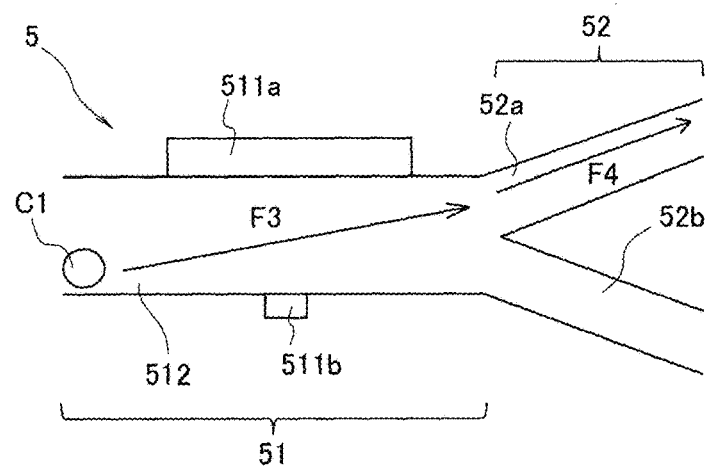
C
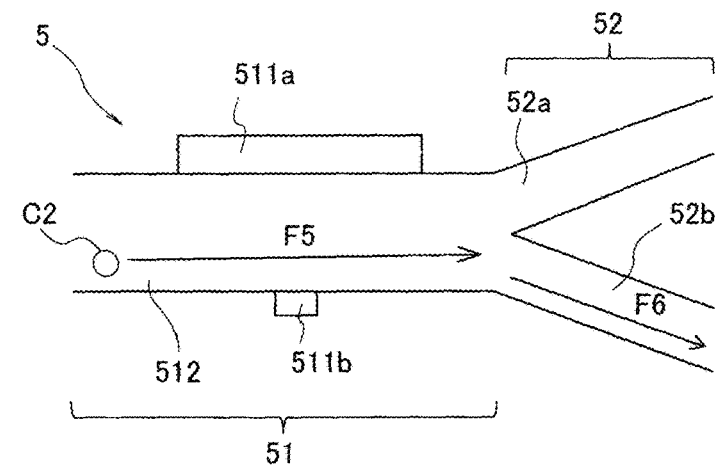

FIG. 10
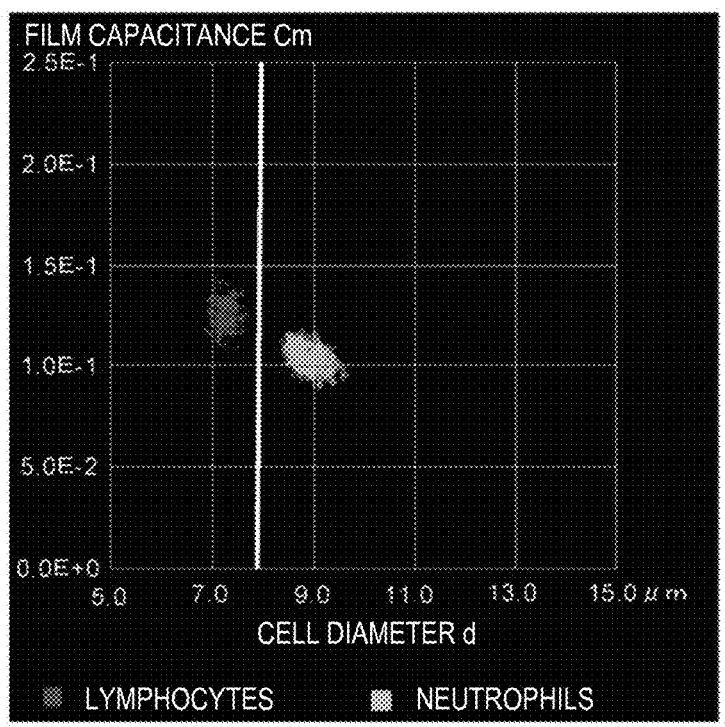
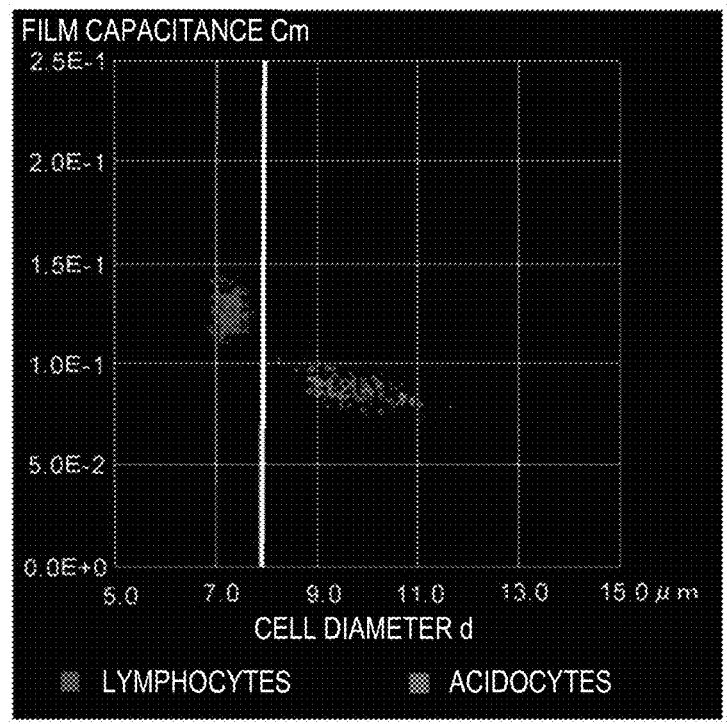

FIG. 11
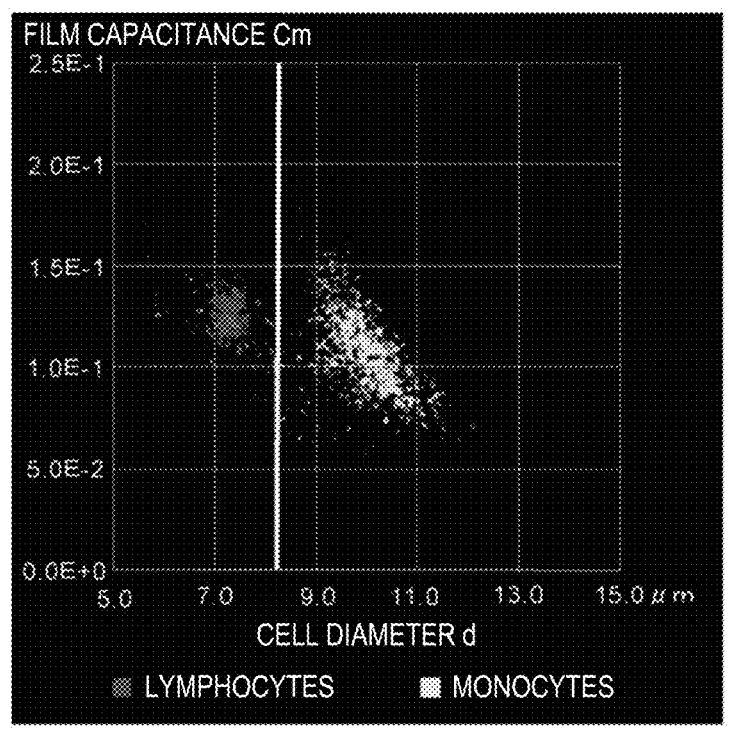
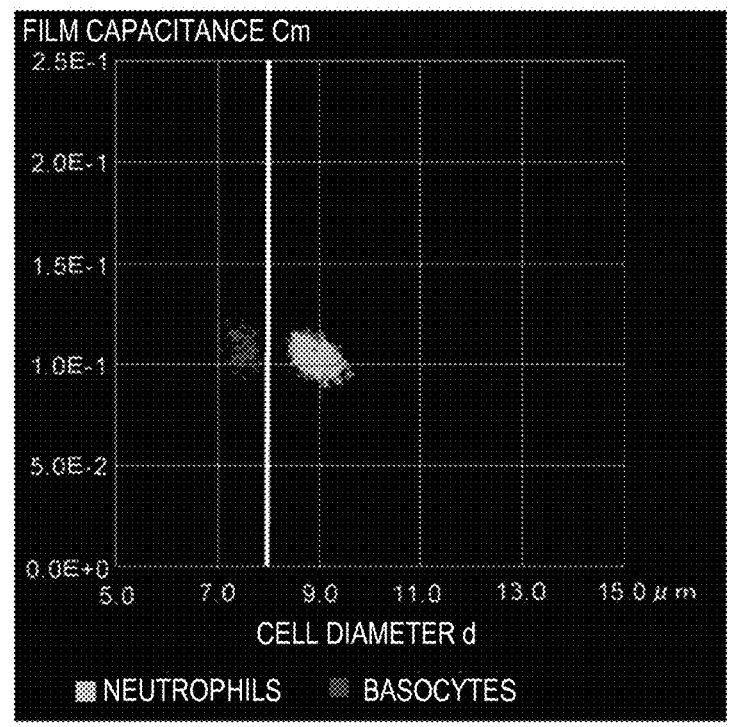

FIG. 12
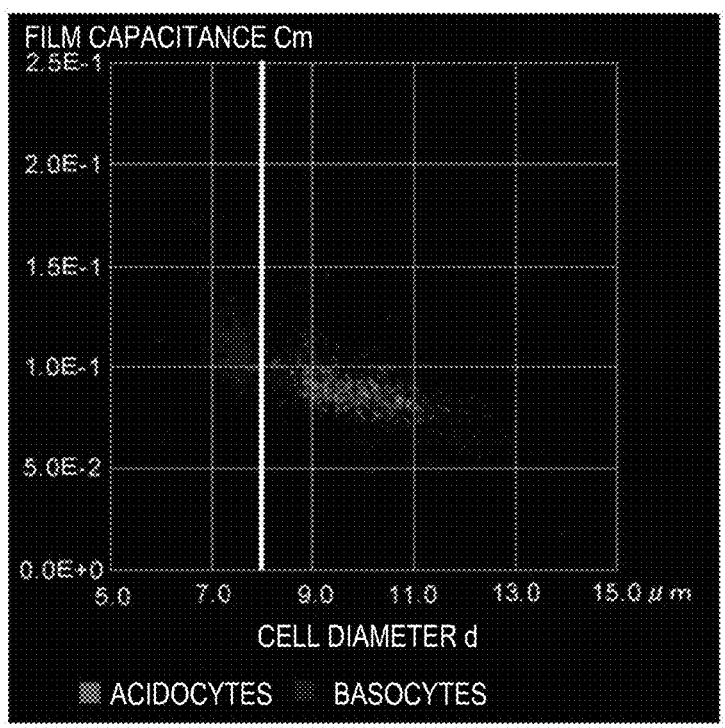
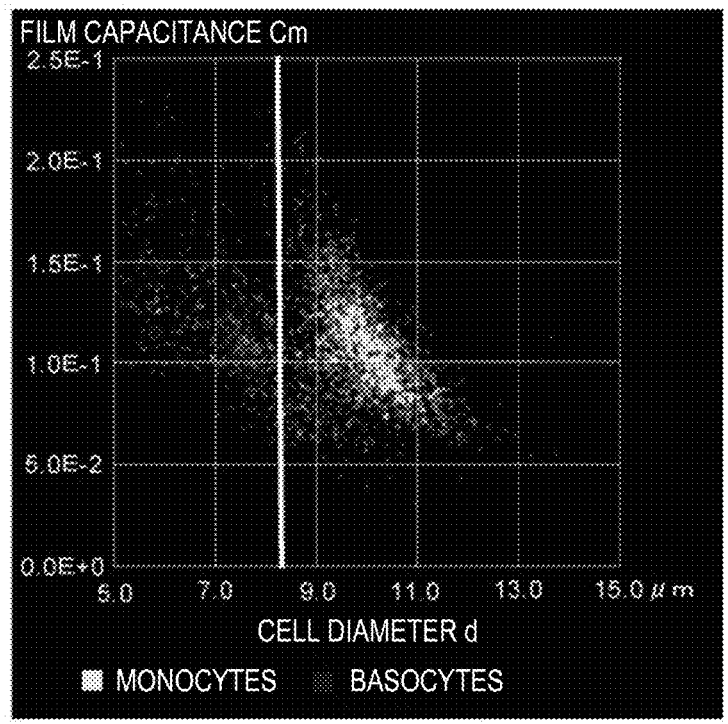

FIG. 13
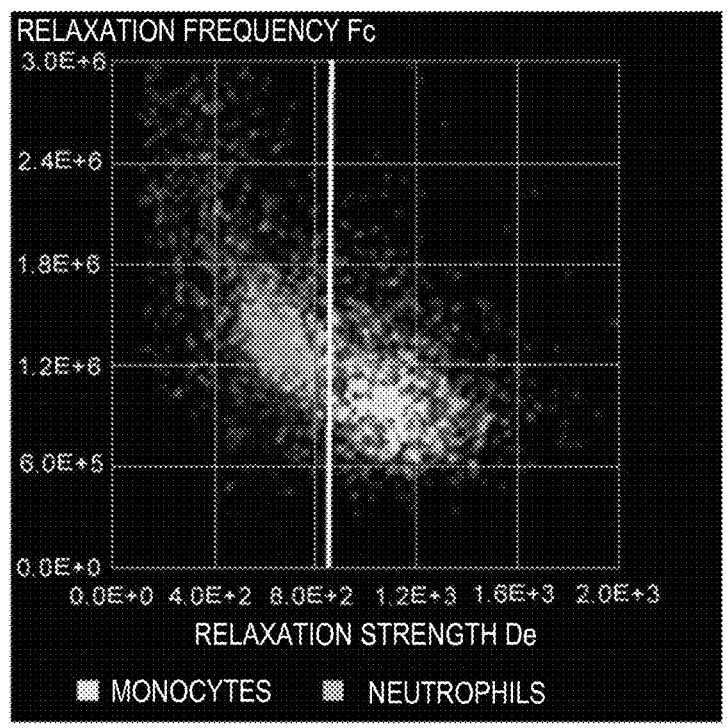
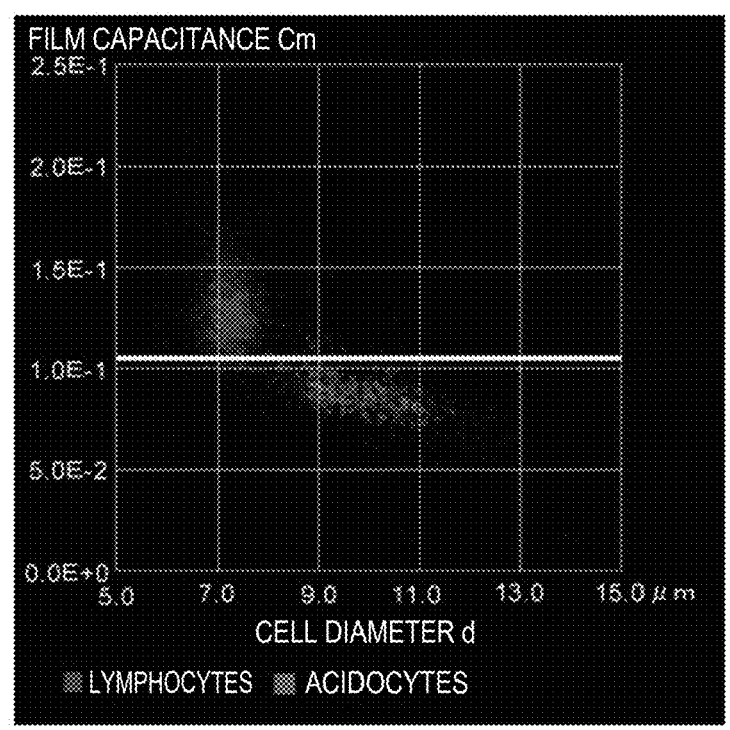

FIG. 18
A
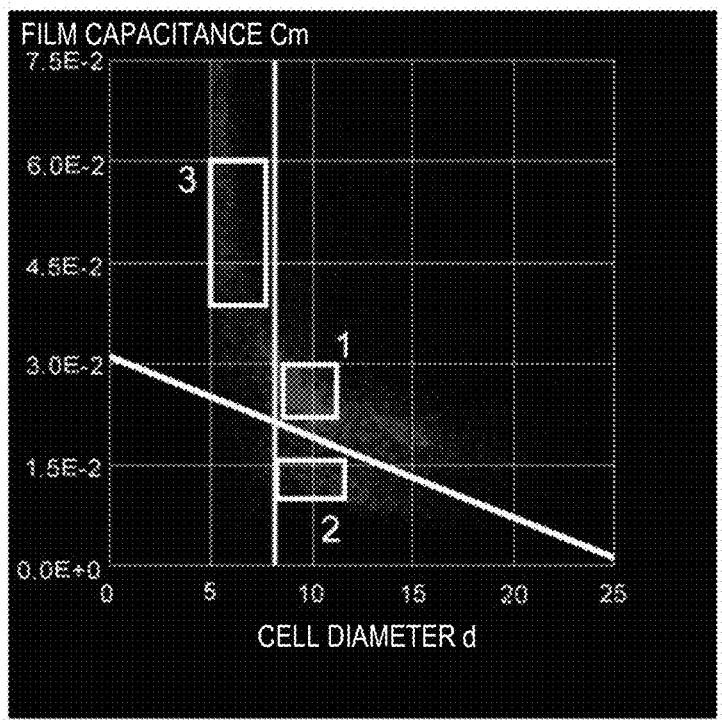
B
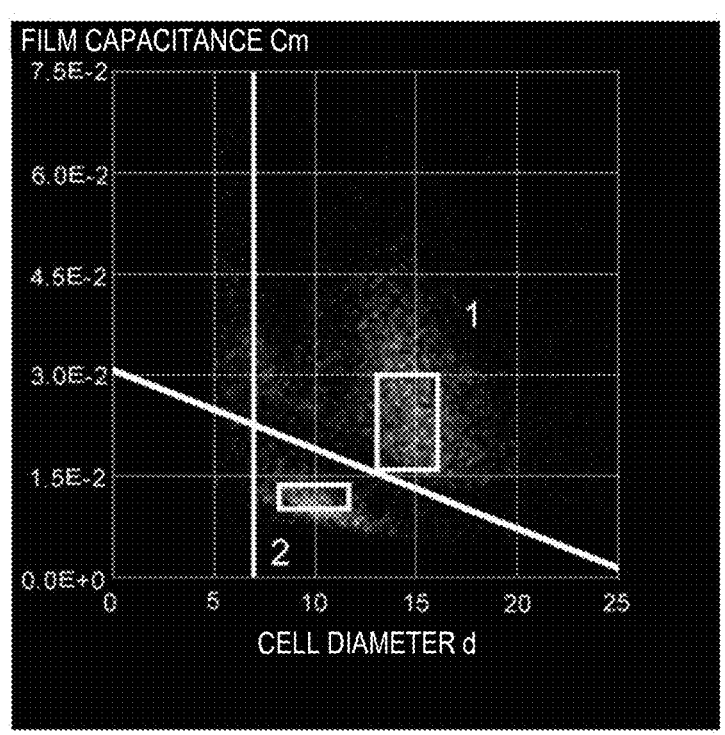

FIG. 19
A
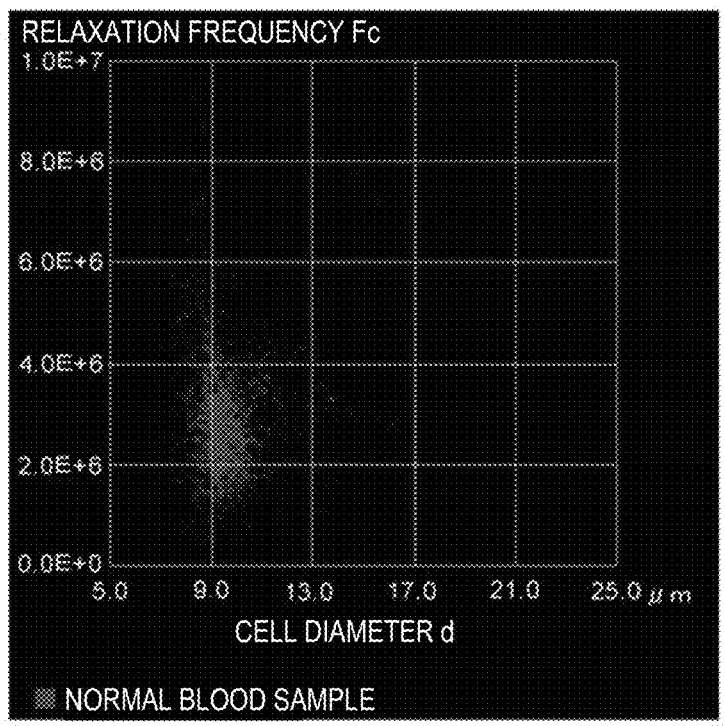
B
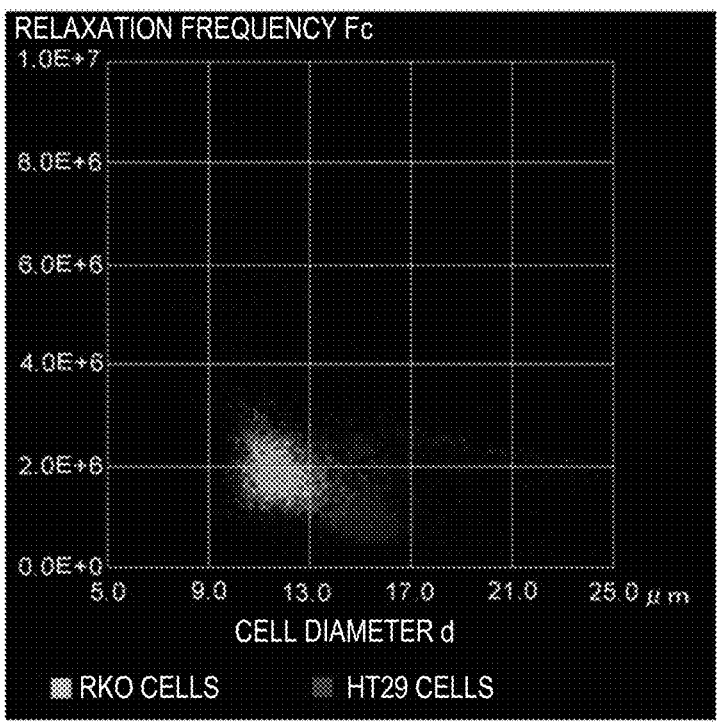

CELL DETERMINATION DEVICE, CELL DETERMINATION SYSTEM, AND CELL DETERMINATION METHOD

TECHNICAL FIELD

The present technology relates to a cell determination device, a cell determination system, a cell determination method, and a cell determination program. More specifically, the present technology relates to a cell determination method and the like based on a feature amount of a complex dielectric constant spectrum.

BACKGROUND ART

In general, cells are known to have different physical properties indicating electric characteristics such as conductivity, permittivity, and electric permittivity according to kinds, states, or the like of the cells. When the permittivity of a cell is measured by sweeping a frequency, a dielectric relaxation property is known to change according to the shape of the cell. Accordingly, devices or the like analyzing cells using such characteristics of the cells have been disclosed.

For example, Patent Literature 1 discloses a blood cell analysis device including "a measurement unit that measures a complex dielectric constant spectrum of a suspension containing one blood cell or a plurality of blood cells and a detection unit that calculates a dielectric variable and/or an electric physical property of the suspension based on the complex dielectric constant spectrum measured by the measurement unit and detects a change in a blood cell state accompanied by drug administration from its calculated value."

The blood cell analysis device can obtain a complex dielectric constant spectrum of a suspension containing blood cells and detect a change in a blood cell state from a dielectric variable or an electric physical property calculated from the complex dielectric constant spectrum.

CITATION LIST

Patent Literature

Patent Literature 1: JP 2011-112497A

SUMMARY OF INVENTION

Technical Problem

In the foregoing blood cell analysis device disclosed in Patent Literature 1, an appropriate expression is selected in accordance with the structure of the blood cell in calculation of the dielectric variables or the electric physical properties from the complex dielectric constant spectrum. However, since the selection of an expression according to a kind of cell results in complex analysis, there has been a demand for a simple model expression for obtaining electric characteristics of a cell. Accordingly, it is desirable to provide a cell determination method and the like based on a complex dielectric constant spectrum in an embodiment of the present technology.

Solution to Problem

The present inventors have found that cells can be classified according to physical properties obtained by applying a simple model expression even to cells which have complex structures, such as "nucleated cells" with nuclei or "aspherical cells" and have accomplished a cell determination method and the like according to the present technology.

That is, the present technology provides a cell determination device including a classification unit configured to classify individual cells based on one of a relaxation strength, a relaxation frequency, and low-frequency conductance obtained from a complex dielectric constant spectrum of the cells.

The classification unit may calculate any one or more of a cell diameter of the cells, film capacitance, and cytoplasm electric conductivity, based on one or more of the relaxation strength, the relaxation frequency, and the low-frequency conductance.

The cell diameter may be calculated based on the low-frequency conductance, the film capacitance may be calculated based on the relaxation strength and the low-frequency conductance, and the cytoplasm electric conductivity may be calculated based on the relaxation strength, the relaxation frequency, and the low-frequency conductance.

The cells may include at least leukocytes, at least myocardial cells, and at least circulation tumor cells.

The cell determination device may further include a measurement unit configured to measure the complex dielectric constant spectrum, or a distribution unit configured to divide the cells into two or more groups based on a signal output by the classification unit.

The present technology also provides a cell determination system including the cell determination device and a cell analysis device including a measurement unit configured to measure the complex dielectric constant spectrum.

The cell analysis device may further include a distribution unit configured to divide the cells into two or more groups based on a signal output by the classification unit.

The present technology also provides a cell determination method including a procedure of classifying, by a classification unit, cells based on one of a relaxation strength, a relaxation frequency, and low-frequency conductance obtained from a complex dielectric constant spectrum of the cells.

The present technology also provides a cell determination program causing a classification unit to perform a function of classifying cells based on one of a relaxation strength, a relaxation frequency, and low-frequency conductance obtained from a complex dielectric constant spectrum of the cells.

Advantageous Effects of Invention

According to the present technology, there are provided the cell determination method and the like of classifying cells according to physical properties based on a complex dielectric constant spectrum.

BRIEF DESCRIPTION OF DRAWINGS

FIG. 3 is a diagram schematically illustrating the configuration of a distribution unit included in the cell determination device according to the first embodiment.

FIGS. 10A and 10B are diagram substitution graphs illustrating distributions of leukocytes based on a cell diameter and film capacitance.

FIGS. 11A and 11B are diagram substitution graphs illustrating distributions of leukocytes based on a cell diameter and film capacitance.

FIGS. 12A and 12B are diagram substitution graphs illustrating distributions of leukocytes based on a cell diameter and film capacitance.

FIGS. 13A and 13B are diagram substitution graphs illustrating distributions of leukocytes based on two kinds of physical properties.

FIGS. 18A and 18B are diagram substitution graphs illustrating distributions of cells containing myocardial cells based on a cell diameter and film capacitance.

FIGS. 19A and 19B are diagram substitution graphs illustrating distributions of cells contained in a normal blood sample, and H29 cells and RKO cells derived from colon cancer based on a cell diameter and a relaxation frequency.

DESCRIPTION OF EMBODIMENTS

Hereinafter, preferred embodiments for carrying out the present technology will be described. The embodiments to be described below are representative embodiments of the present technology and the scope of the present technology is not construed narrowly due to the embodiments. The description will be made in the following order.

Figure 1:
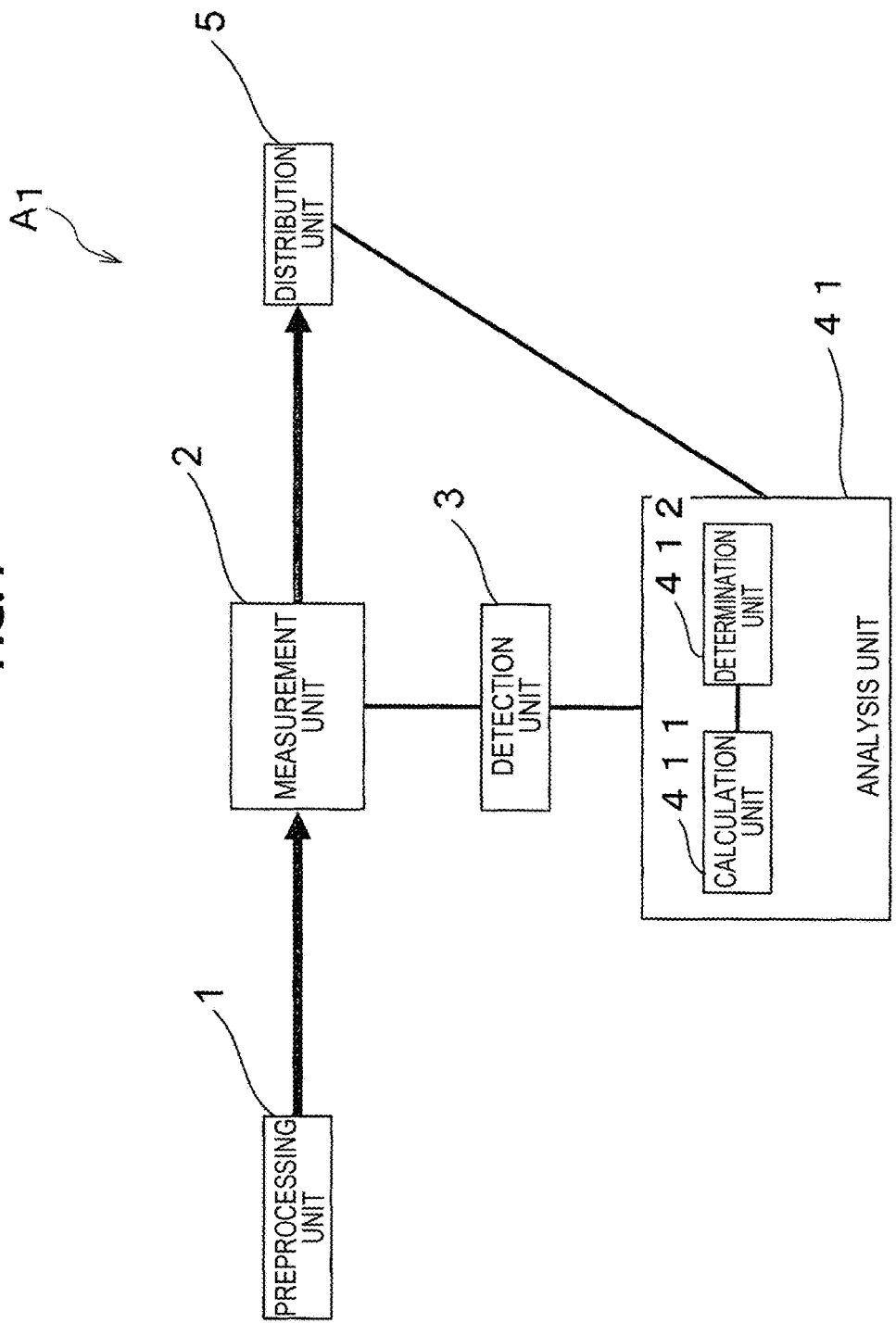
FIG. 1 is a block diagram illustrating the configuration of a cell determination device according to a first embodiment of the present technology.

1. Cell determination device according to a first embodiment of the present technology
   (1) Preprocessing unit
   (2) Measurement unit
   (3) Detection unit
   (4) Analysis unit
   (5) Distribution unit
2. Operation of the cell determination device according to an embodiment of the present technology
   (1) Cell suspension preparation procedure
   (2) Complex resistance measurement procedure
   (3) Cell-derived signal detection procedure
   (4) Physical property calculation procedure
   (5) Cell classification procedure
   (6) Cell distribution procedure
3. Cell determination device according to a second embodiment of the present technology
4. Cell determination system according to an embodiment of the present technology
5. Specific examples of cells classified by a cell determination device
   (1) Leukocytes
   (2) Myocardial cells
   (3) Circulating tumor cells
6. Cell determination method and cell determination program according to an embodiment of the present technology 1. Cell Determination Device According to a First Embodiment of the Present Technology FIG. 1 is a block diagram illustrating a cell determination device according to an embodiment of the present technology. In FIG. 1, a cell determination device denoted by reference sign A1 broadly includes a preprocessing unit 1, a measurement unit 2, a detection unit 3, an analysis unit 41, and a distribution unit 5. Each configuration of the cell determination device A1 will be described in order. In FIG. 1, an arrow indicates a direction in which a liquid (cell suspension) containing cells flows.

(1) Preprocessing Unit

The preprocessing unit 1 is configured to prepare a cell suspension in a state suitable for measurement of complex resistance in the measurement unit 2 to be described below by processing a sample. For example, when a measurement target is leukocytes, the preprocessing unit 1 has a configuration necessary for a hemolytic process or density gradient centrifugation in order to remove erythrocytes, thrombocytes, and the like contained in the whole blood. In the configuration, for example, a temperature adjustment mechanism, a centrifuge, a filter for filtration, or the like for a sample can be included. In the cell determination device A1 according to an embodiment of the present invention, the preprocessing unit 1 is not an essential constituent. A sample processed in advance by a user can also be used in measurement of cells in the cell determination device A1.

(2) Measurement Unit

The measurement unit 2 is configured to measure complex resistance of a cell which is a measurement target of the cell determination device 1. The measurement unit 2 includes a flow passage through which a cell suspension is circulated, a pair of electrodes which are disposed in the flow passage, and an impedance analyzer which measures impedance between the electrodes disposed in the flow passage at a plurality of frequencies. A stricture portion through which cells can pass one by one is preferably formed in the flow passage.

Figure 2:
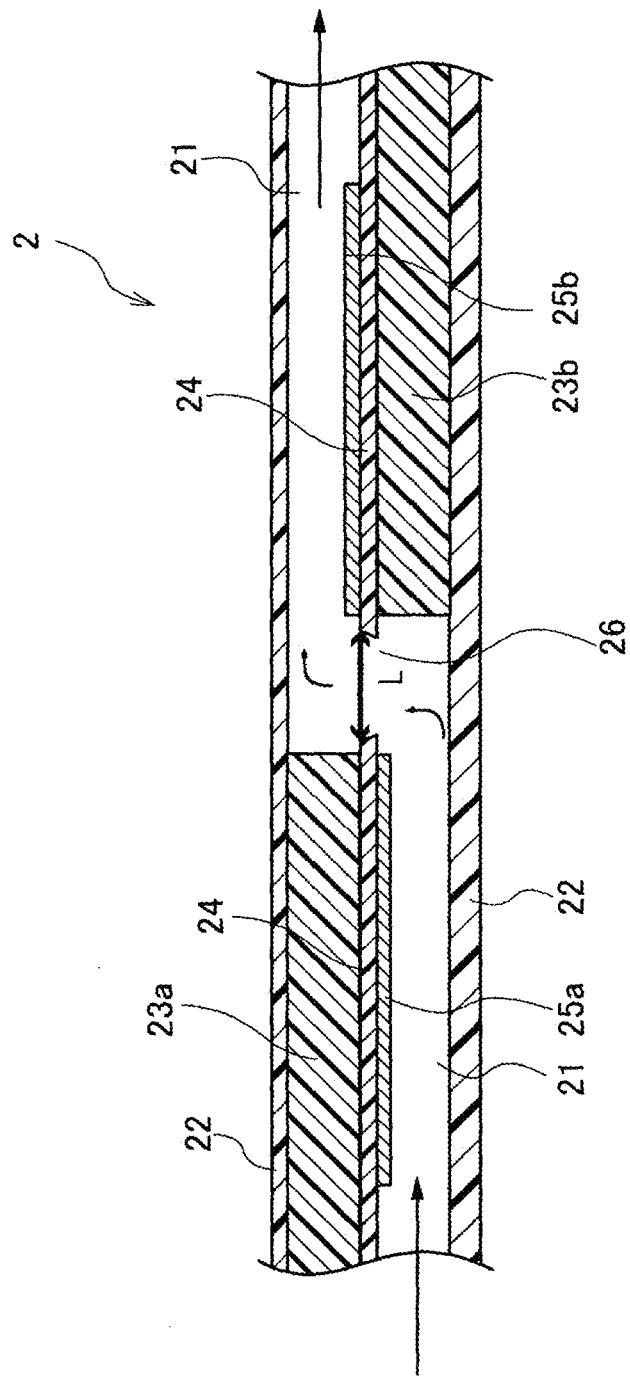
FIG. 2 is a diagram schematically illustrating the configuration of a flow passage formed in the cell determination device according to the first embodiment.

FIG. 2 is a sectional view illustrating an example of the configuration of the flow passage formed in the measurement unit 2 according to the embodiment. Arrows in the drawing indicate a direction in which the cell suspension flows. A flow passage 21 formed in the measurement unit 2 can be configured such that two flow passage layers 23a and 23b with circulation positions mutually different in the thickness direction communicate with each other via a stricture portion 26. Specifically, two cover layers 22 formed of a polyimide or the like, a pair of electrodes 25a and 25b, an intermediate layer 24 having the stricture portion 26, and the two flow passage layers 23a and 23b in which the flow passage 21 is formed are stacked.

The pair of electrodes (the electrodes 25a and 25b) in the intermediate layer 24 are formed on both surfaces at positions on both sides of the stricture portion 26. Flow passage portions (the flow passage 21) of the two flow passage layers 23a and 23b through which the cell suspension is circulated communicate with each other via the stricture portion 26 formed in the intermediate layer 24. The stricture portion 26 has a size through which the cells contained in the cell suspension can pass one by one. For example, in terms of measurement sensitivity and flow stability, it is suitable to set the size of the stricture portion so that the size of the stricture portion is twice to three times the average diameter of the target cells. A length L of the stricture portion 26 is preferably in the range of 20 μm to 35 μm, for example, when the cell suspension contains myocardial cells or circulating tumor cells. The length L is preferably in the range of 13 μm to 20 μm, for example, when the cell suspension contains leukocytes.

The measurement unit 2 may be connected to a liquid-supply unit (the liquid-supply unit is not illustrated in FIGS. 1 and 2) that stably supplies the cell suspension to the flow passage 21. The liquid-supply unit includes a liquid-supply pump that supplies the cell suspension to the flow passage 21 and a container that contains the cell suspension. The liquid-supply unit stably supplies the cell suspension to a flow passage device at a flow rate at which the cells are present in the stricture portion 26 of the flow passage 21 for a time which is twice or more a sampling interval of the foregoing impedance analyzer. When the cells in the flow passage are moved at such a speed, an influence of the flow rate on a measurement result becomes negligible.

(3) Detection Unit

The detection unit 3 is configured to detect a signal originating from a cell among signals output from the above-described measurement unit 2. The detection unit 3 can be configured by a general computer including a CPU, a memory, and a hard disk. The hard disk stores, for example, an OS and a computer program processing measurement data output by the measurement unit 2. The detection unit 3 may also be configured by hardware such as a field-programmable gate array (FPGA). In the cell determination device A1 according to an embodiment of the present technology, the detection unit 3 is not an essential constituent. For example, the impedance analyzer or the like included in the measurement unit 2 may be configured to have the function of the detection unit 3.

(4) Analysis Unit

The analysis unit 41 illustrated in FIG. 1 includes a calculation unit 411 that calculates a complex dielectric constant spectrum from the complex resistance measured by the above-described measurement unit 2 and calculates physical properties from characteristic amounts of the complex dielectric constant spectrum and a determination unit 412 that classifies the cells into two or more groups based on the physical properties. The analysis unit 41 can be configured by a general computer including a CPU, a memory, and a hard disk. The hard disk stores, for example, an OS and a cell determination program to be described below. In FIG. 1, the calculation unit 411 and the determination unit 412 are included in the same analysis unit 41. However, the calculation unit 411 and the determination unit 412 may be configured as separate units.

(5) Distribution Unit

The distribution unit 5 is configured to divide the cells into cells classified as a distribution target and cells classified as cells other than the distribution target. For example, the distribution unit 5 includes a branch flow passage which distributes cells to the downstream side of the stricture portion 26, a mechanism which selectively moves circulated cells to a predetermined branch flow passage according to a determination result of the above-described determination unit 412, and a cell storage unit which stores the cells circulated through the branch flow passage. A plurality of branch flow passages and a plurality of cell storage units can also be disposed in the distribution unit 5 so that two or more kinds of cells are distributed. In the cell determination device A1 according to an embodiment of the present technology, the distribution unit 5 is not an essential constituent. For example, when the cell determination device A1 is used for only cell classification, the distribution unit 5 may not be included in the cell determination device A1.

As the mechanism which selectively moves cells to a predetermined branch flow passage, for example, a configuration of the related art used in a flow cytometer or the like can also be adopted. For example, when a distribution target is selected from two or more kinds of cells which can be classified based on a cell diameter d to be described below, a configuration for controlling flow of cells using a dielectrophoretic force may be installed in the distribution unit 5.

In the distribution unit 5 illustrated in FIGS. 3A to 3C, an electric field application unit 51 including electrodes 511a and 511b that generate a dielectrophoretic force are installed. After a cell C which is a distribution target or a cell other than the distribution target flows through a flow passage 512 (see an arrow F1) formed between the electrodes 511a and 511b, the cell is circulated through either of the flow passages 52a and 52b that form a branch flow passage 52 (see an arrow F2).

As illustrated in FIG. 3B, when an electric field is applied by the electric field application unit 51, the dielectrophoretic force is applied, a movement direction of a cell C1 with a cell diameter greater than a predetermined cell diameter is changed by the electric field application unit 51 (see an arrow F3), and the cell C1 is circulated through the predetermined flow passage 52a (see an arrow F4) in the branch flow passage 52. As illustrated in FIG. 3C, since an influence of the dielectrophoretic force on a cell C2 with a cell diameter less than the predetermined cell diameter is small, a movement direction of the cell C2 is not sufficiently changed by the electric field application unit 51 (see an arrow F5), and thus the cell C2 is circulated through the predetermined flow passage 52B of the branch flow passage 52 (see an arrow F6).

The dielectrophoretic force can be expressed by the following expressions (1) and (2).

[Math 1]

$$F_{DEP} = 2\pi r^3 \varepsilon_M \text{Re}[K(\omega)] \nabla E^2 \tag{1}$$

-continued

[Math 2]

$$V = \frac{a(\rho_s - \rho)r^2}{18\mu} \quad (2)$$

In the expressions, r indicates a radius of a particle (cell), ∈M indicates the permittivity of a medium, K(ω)) indicates a Clausius-Mossotti function, E indicates the intensity of an electric field, a indicates acceleration, ρ indicates the density of the medium, and μ indicates the viscosity of the medium.

As expressed in equation (1), the dielectrophoretic force is generated in a form proportional to a cube of the radius of a particle and a final speed of a particle in a liquid reaches a Stoke expression proportional to a square of the radius of the particle, as expressed in expression (2). Therefore, a movement amount of a particle with a larger particle diameter is larger when the dielectrophoretic force is applied for the same action time. Accordingly, by setting an alternating-current voltage generating the dielectrophoretic force to be in a range in which a movement amount is not sufficient for a particle (cell) with a diameter less than a predetermined cell diameter, cells can be divided into cells of a distribution target and cells other than the distribution target in the distribution unit 5.

Figure 4:
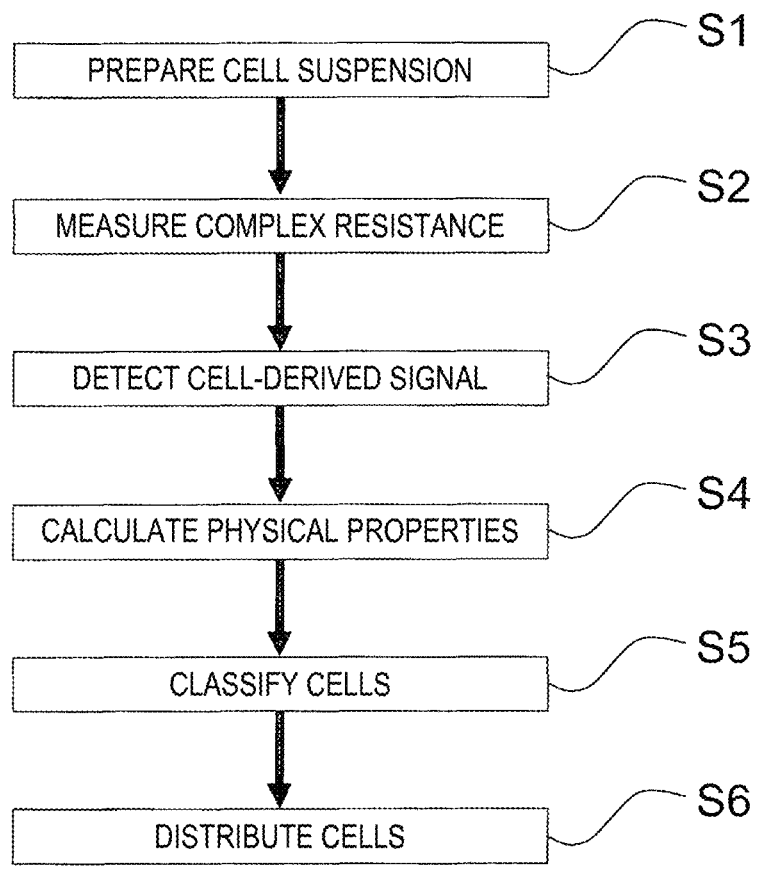
FIG. 4 is a flowchart illustrating an operation of the cell determination device according to an embodiment of the present technology.

2. Operation of Cell Determination Device According to Embodiment of the Present Technology Next, an operation of the cell determination device A1 according to an embodiment of the present technology will be described with reference to the flowchart illustrated in FIG. 4. As illustrated in the flowchart (FIG. 4), the cell determination method according to an embodiment of the present technology includes a cell suspension preparation procedure S1, a complex resistance measurement procedure S2, a cell-derived signal detection procedure S3, a physical property calculation procedure S4, a cell classification procedure S5, and a cell division procedure S6.

(1) Cell Suspension Preparation Procedure

In the cell suspension preparation procedure S1, a sample containing cells is prepared so that the sample is suitable for measurement of complex resistance using the cell determination device A1. Cell which are a measurement target using the cell determination device A1 according to an embodiment of the present technology are not particularly limited. Examples of the cells include blood cells such as leukocytes and erythrocytes, myocardial cells, fibroblasts, endothelial cells, and circulating tumor cells. The cells may be cultivated cells.

For example, when cells are leukocytes, cells that are not the measurement target such as erythrocytes or thrombocytes are moved by performing a hemolytic process, density-gradient centrifugation, or a process by a hemagglutination reagent on the whole blood in the present procedure S1. In order to prevent obstruction of the above-described stricture portion 26, it is preferable to remove particles more minute than the target cells from the sample using a physical filter such as a membrane or a filter paper in the present procedure S1. Further, when cells contained in a blood sample that contains circulating tumor cells are classified, leukocytes and erythrocytes may be removed in advance using an antibody in the present procedure S1.

In order to circulate the cells through the flow passage 21 of the above-described measurement unit 2, the cells are preferably prepared in a "cell suspension" dispersed by a solvent. The solvent is not particularly limited as long as the solvent has a composition in which measurement in the complex resistance measurement procedure S2 to be described below or the like is not inhibited. An example of the solvent is physiological saline. Further, EDTA or fetal bovine serum (FBS) with a density of about 2% may also be contained in the physiological saline.

(2) Complex Resistance Measurement Procedure

In the complex resistance measurement procedure S2, by applying a voltage to the electrodes 25a and 25b of the above-described measurement unit 2, an amplitude and a phase are measured for a change in complex resistance occurring when one of the cells contained in the cell suspension obtained in the cell suspension preparation procedure S1 passes through the stricture portion 26. The measurement unit 2 measures the complex resistance of the cell throughout multi-point frequencies (for example, 16 points) in a frequency range in which a cell dielectric relaxation phenomenon occurs for the cells flowing one by one in the flow passage. The frequency used for the measurement can be set in the range of, for example, 100 kHz to 100 MHz.

In order to obtain a complex dielectric constant spectrum, it is necessary to measure the complex resistance throughout the multi-point frequencies within a time in which the cells passes through the stricture portion 26. Therefore, a method of estimating the complex resistance at each frequency by combining input voltages with a plurality of frequencies in a superimposition manner to apply the input voltages between the electrodes by a circuit based on a general IV method and performing a Fourier transform on output voltages and output currents may also be used. A frequency at which a cell shows dielectric relaxation is in the range of about 100 kHz to about 10 MHz. In the present procedure S2, the measured complex resistance is output as a signal to the detection unit 3.

(3) Cell-Derived Signal Detection Procedure

In the cell-derived signal detection procedure S3, a change in the complex resistance when the cells pass through the stricture portion 26 in the complex resistance output from the measurement unit 2 to the detection unit 3 in the complex resistance measurement procedure S2 is detected. That is, the cell suspension is circulated through the flow passage 21 of the measurement unit 2 and a portion corresponding to a "cell-derived signal" changed with the passing of the cell is extracted from the continuously measured complex resistance.

In order to extract the portion derived in the cell from the measurement complex resistance, a threshold value for the complex resistance may be set, for example, in consideration of a liquid-supply condition in the measurement unit 2, the size of the stricture portion 26, a kind of detection target cell, the density of the cells in the cell suspension, and the like. The signal detected in the present procedure S3 is output to the calculation unit 411 of the analysis unit 41.

(4) Physical Property Calculation Procedure

In the physical property calculation procedure S4, the calculation unit 411 calculates the physical properties of the cell from the cell-derived signal detected by the detection unit 3 in the cell-derived signal detection procedure S3. The physical property calculation procedure S4 is as follows.

In the present procedure S4, the calculation unit 411 first converts the cell-derived complex resistance obtained in the cell-derived signal detection procedure S3 into a complex dielectric constant according to a method of the related art. Next, a complex dielectric constant spectrum is obtained from the complex dielectric constant. Then, the calculation unit 411 calculates the physical properties from the feature amounts of the complex dielectric constant spectrum.

Examples of the physical properties include a cell diameter d, film capacitance Cm, cytoplasm electric conductivity K, a relaxation strength De, a relaxation frequency Fc, and low-frequency conductance $G_{low}$. Any or one or more of the physical properties is calculated.

Figure 5:
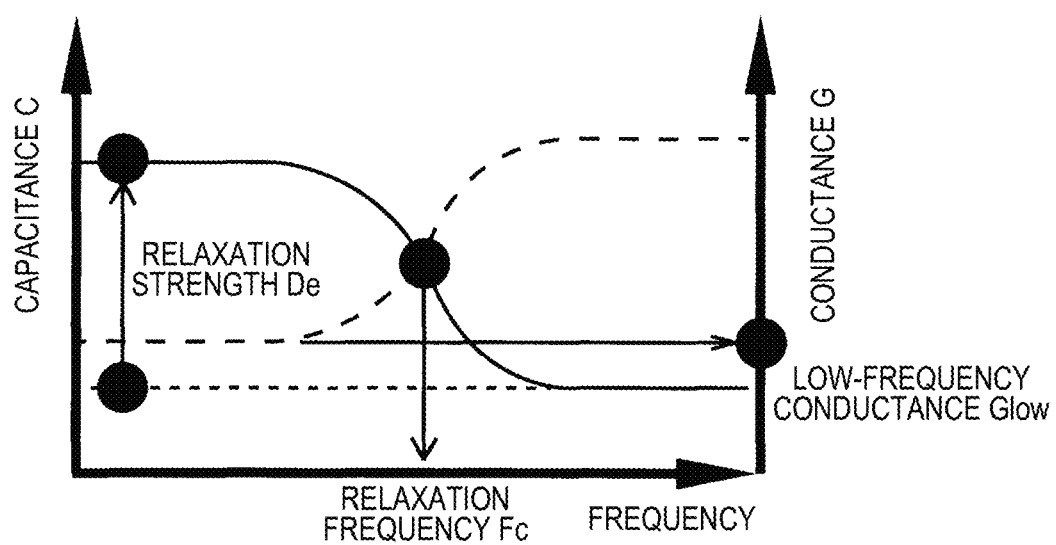
FIG. 5 is a diagram substitution graph schematically illustrating a relaxation strength, a relaxation frequency, and a low-frequency conductance obtained from a complex dielectric constant spectrum of cells.

In the present procedure S4, of the physical properties, the relaxation strength De, the relaxation frequency Fc, or the low-frequency conductance $G_{low}$ is first calculated from the complex dielectric constant spectrum. FIG. 5 schematically illustrates the relaxation strength De, the relaxation frequency Fc, and the low-frequency conductance $G_{low}$ obtained from the complex dielectric constant spectrum. The low-frequency conductance $G_{low}$ is electric conductivity based on the complex resistance of a low frequency. In the cell determination method according to an embodiment of the present technology, the "low frequency" of the low-frequency conductance $G_{low}$ can be a frequency predetermined to be lower than the relaxation frequency Fc in accordance with the configuration of the measurement unit 2 or the like. In the cell determination method according to an embodiment of the present technology, the low frequency is preferably equal to or less than, for example, 500 kHz. As illustrated in FIG. 5, a frequency at the limit value of the low capacitance may be the "low frequency."

Subsequently, the calculation unit 411 calculates one or more of the cell diameter d, the film capacitance Cm, and the cytoplasm electric conductivity K based on one or more of the calculated relaxation strength De, relaxation frequency Fc, and low-frequency conductance $G_{low}$. These physical properties can also be calculated by single relaxation expressions obtained by modeling a simple spherical cell. In the single relaxation expressions, for example, the cell diameter d is calculated based on the low-frequency conductance $G_{low}$, the film capacitance Cm is calculated based on the relaxation strength De and the low-frequency conductance $G_{low}$, and the cytoplasm electric conductivity K is calculated based on the relaxation strength De, the relaxation frequency Fc, and the low-frequency conductance $G_{low}$. In the cell determination method according to an embodiment of the present technology, the expression obtained by modeling the simple spherical cell is also applied to determination of "nucleated cells" with nuclei or "aspherical cells" with a shape which is not simply spherical. Examples of the "aspherical cells" include an erythrocyte of which a part of the cell is recessed and an echinocyte with a protrusion.

The single relaxation expressions obtained by modeling the foregoing simple spherical cells are, for example, the following expressions (3) to (5). The cell diameter d, the film capacitance Cm, and the cytoplasm electric conductivity K can be calculated by the following expressions (3) to (5).

[Math 3]
$$d = \left(\frac{G_{low}}{a}\right)^{\frac{1}{b}} \quad (3)$$

[Math 4]
$$C_m = \frac{De}{d^4} \quad (4)$$

[Math 5]
$$K = C_m d Fc \quad (5)$$

In the expressions, d indicates a cell diameter, $G_{low}$ indicates low-frequency conductance, Cm indicates film capacitance, De indicates a relaxation strength, K indicates cytoplasm electric conductivity, and Fc indicates a relaxation frequency. Integers a and b in expression (3) are parameters that depend on the configuration of the flow passage 21 of the measurement unit 2. Therefore, the values of the integers a and b can be calculated from the shape of the stricture portion 26. In practice, polyethylene beads or the like of which the spherical shape is precisely managed can be measured by the cell determination device A1 and the values of the integers a and b can be calculated. For the simple relaxation expressions obtained by modeling the simple spherical cell, the foregoing expressions (3) to (5) can be appropriately modified and used.

(5) Cell Classification Procedure

In the cell classification procedure S5, the determination unit 412 classifies the individual cells based on the physical properties calculated in the physical property calculation procedure S4. Specifically, the cells contained in the cell suspension are classified into two or more groups based on the physical properties of two or more kinds of cells contained in the cell suspension.

Figure 6:
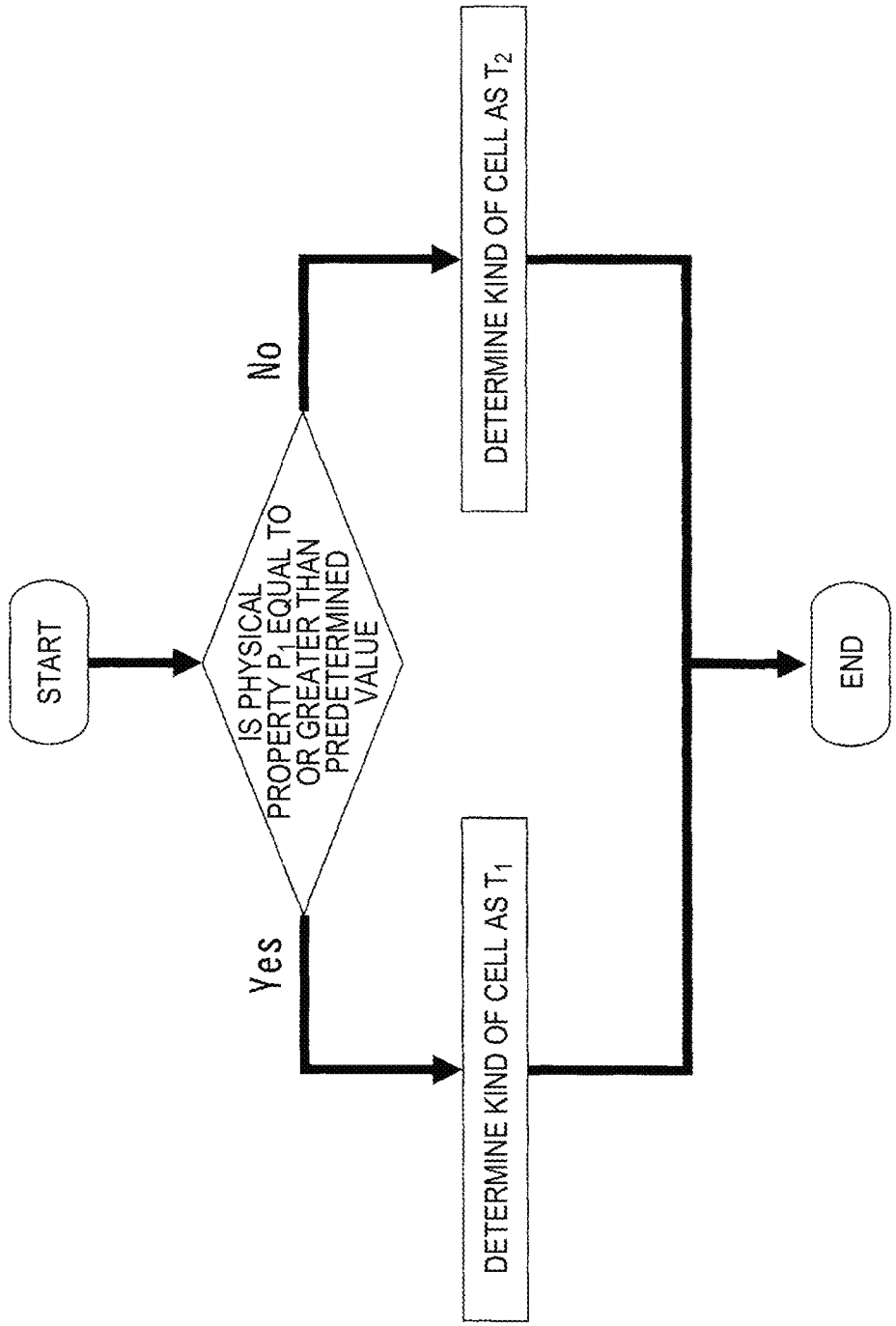
FIG. 6 is a flowchart illustrating a classification procedure of cells in a determination unit.

The classification of the cells by the determination unit 412 will be described with reference to FIG. 6. As illustrated in FIG. 6, in the present procedure S5, for example, a predetermined value is determined for any one physical property $P_1$. A method of determining the predetermined value will be described below. When the physical property $P_1$ of each cell calculated in the physical property calculation procedure S4 is equal to or greater than the predetermined value, the cell is classified as one kind $T_1$ (or into one group). Conversely, when the physical property $P_1$ of the cell is less than the predetermined value, the cell is classified as another kind $T_2$ (or into another group).

Figure 7:
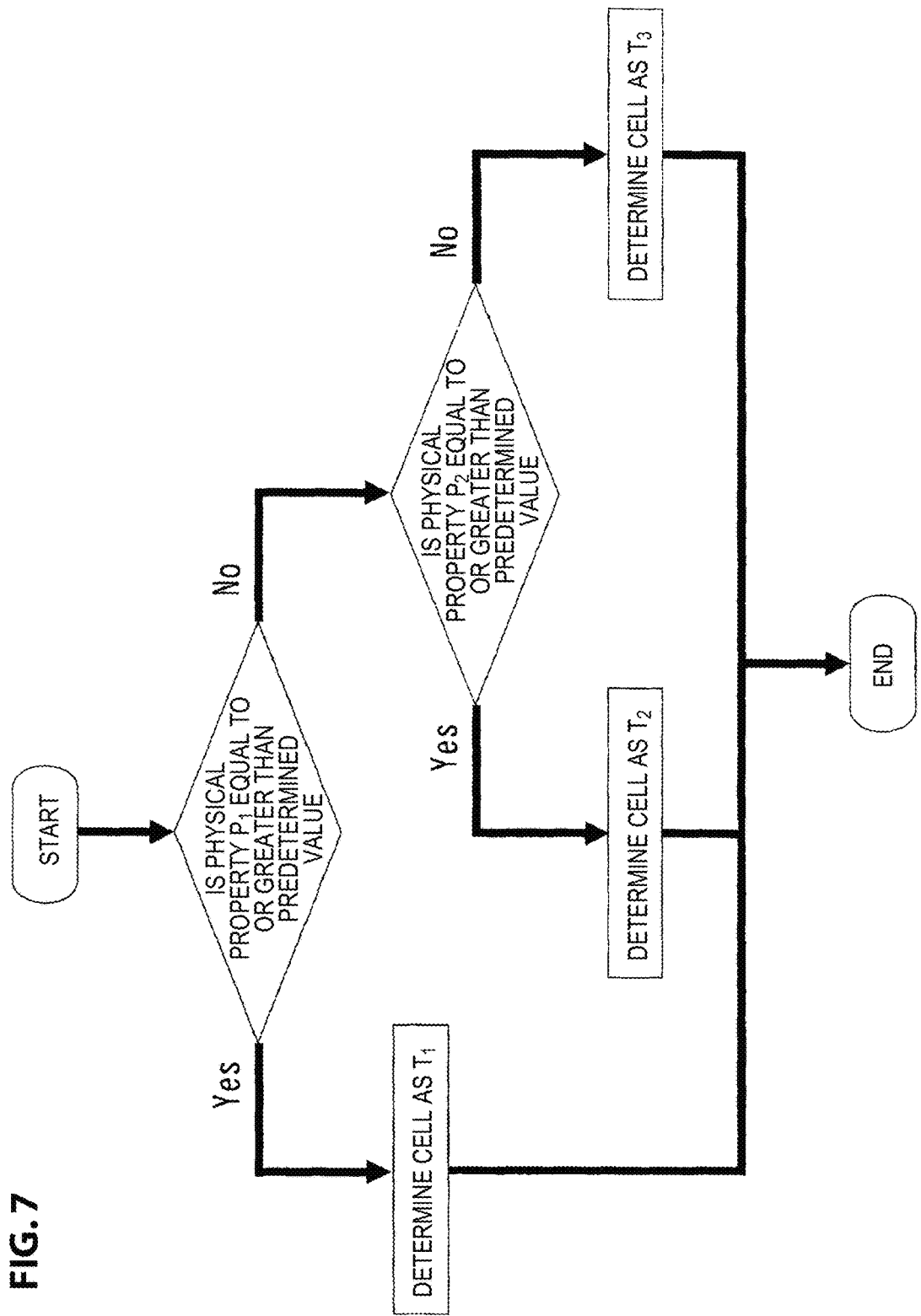
FIG. 7 is a flowchart illustrating a classification procedure of cells in a determination unit.

When the cells are classified as three kinds of cells or into three groups, two kinds of physical properties $P_1$ and $P_2$ may be used. As illustrated in FIG. 7, when the cells are classified as three kinds of cells, the cells are first classified into two groups according to whether the physical property $P_1$ of each cell is equal to or greater than the predetermined value. Thereafter, the cells belonging to any one group are classified into two groups using another physical property $P_2$ according to whether the physical property $P_2$ is equal to or greater than a predetermined value. As a result, the cells are classified into three groups. The kinds of physical properties used for the classification in the cell classification procedure S5 may be one or more kinds of physical properties and are not particularly limited. In order to classify the cells, a function that uses two or more selected physical properties as variables may be used.

In FIGS. 6 and 7, the cells are classified into two or more groups according to whether the physical properties $P_1$ and $P_2$ are equal to or greater than the predetermined value or are less than the predetermined value. However, when the cells are classified into two groups, the cells may be classified into one group for which the physical properties are greater than the predetermined value and one group for which the physical properties are equal to or less than the predetermined value. The predetermined value may not be included in either of the two groups.

In the cell classification procedure S5, the predetermined value of the physical properties for classifying the cells may be determined from, for example, a distribution of the calculated physical properties of each cell. Specifically, a one-dimensional histogram based on one physical property, a two-dimensional scatter diagram based on two physical properties, a three-dimensional scatter diagram based on three physical properties, or the like is generated using the physical properties calculated for each cell. Then, a predetermined value of the physical properties delimiting two or more regions in the diagram is determined according to the distribution of the cell shown in the diagram. To determine a boundary for delimiting the region, a technology for gate setting used in a flow cytometer of the related art can be used.

The boundary of the region used to classify the cells may be determined for each use of the cell determination device A1, but information regarding a previously determined boundary may be recorded in the determination unit 412 and the information regarding the boundary may be read in the cell classification procedure S5. Thus, when the cells are analyzed and distributed under the same conditions, a work of selecting and reading the previous information is merely performed for the setting of the boundary in the determination unit 412. Thus, a burden on a user can be reduced, and thus the cell classification procedure S5 becomes more efficient.

In the cell classification procedure S5, the determination unit 412 performs the classification of the cells in real time. When the classified cells are a distribution target, a signal may be output to operate the distribution unit 5.

(6) Cell Distribution Procedure

In the cell distribution procedure S6, the distribution unit 5 receiving a distribution signal output from the determination unit 412 is operated to circulate the distribution target cells to a predetermined branch flow passage. When the distribution target cells are circulated to respective cell storage units, the distribution unit 5 is operated to circulate each cell to a predetermined branch flow passage according to the result of the above-described cell classification procedure S5.

According to the cell determination method according to an embodiment of the present technology, the cells can be classified based on the calculated physical properties. Therefore, for example, it is not necessary to dye the cells in association with use of optical system flow cytometry. When preprocessing of the cells, such as dyeing, is not necessary, an influence of the preprocessing on the cells can be reduced. Therefore, the cells distributed after the classification by the cell determination device A1 according to an embodiment of the present technology are easily used for subsequent analysis or cultivation.

According to the cell determination method according to an embodiment of the present technology, it is possible to obtain the physical properties effective for the classification of the cells by the expressions obtained by modeling the simple spherical cell without selecting a physical property calculation method in accordance with morphological characteristics or the like of the cells.

Figure 8:
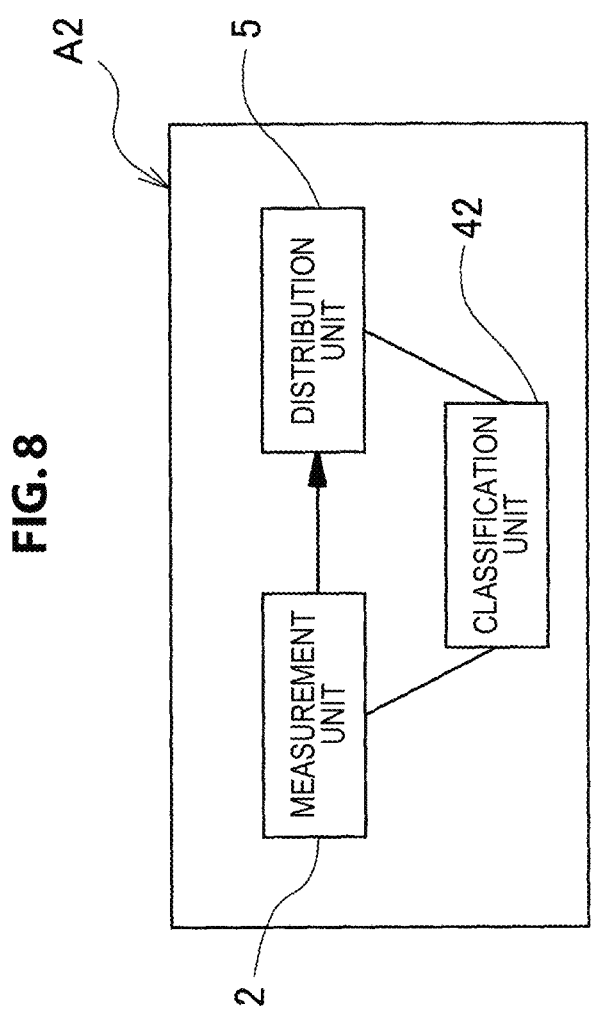
FIG. 8 is a block diagram illustrating the configuration of a cell determination device according to a second embodiment of the present technology.

3. Cell Determination Device According to Second Embodiment of the Present Technology FIG. 8 is a block diagram illustrating a cell determination device according to a second embodiment of the present technology. An arrow illustrated in FIG. 8 indicates a direction in which a liquid (cell suspension) containing cells flows, as in FIG. 1. A cell determination device denoted by reference sign A2 in FIG. 8 includes a classification unit 42 as one form of the analysis unit 41 in the cell determination device A1 according to the first embodiment. The classification unit 42 classifies individual cells based on any one of a relaxation strength De, a relaxation frequency Fc, and low-frequency conductance $G_{low}$ obtained from a complex dielectric constant spectrum of the cells. That is, the classification unit 42 has the function of classifying the cells of the above-described determination unit 412. The classification unit 42 may have a function of calculating a cell diameter d, film capacitance Cm, or cytoplasm electric conductivity K based on one or more of the relaxation strength De, the relaxation frequency Fc, and the low-frequency conductance $G_{low}$ obtained from the complex dielectric constant spectrum. That is, the classification unit 42 may have the function of calculating the physical properties of the above-described calculation unit 411. Further, a pre-measured complex dielectric constant spectrum or the relaxation strength De, the relaxation frequency Fc, or the low-frequency conductance $G_{low}$ of this complex dielectric constant spectrum may be stored in the cell determination device A2. The classification unit 42 can also classify the cells using the complex dielectric constant spectrum or the physical property stored in the cell determination device A2.

The cell determination device A2 according to the second embodiment may include a measurement unit 2 that measures the complex dielectric constant spectrum of determination target cells. The cell determination device A2 may include a distribution unit 5 that divides the cells into two or more groups based on a signal output by the classification unit 42. The configurations and the functions of the measurement unit 2 and the distribution unit 5 are the same as those of the cell determination device A1 according to the first embodiment. The same configuration and function as those of the cell determination device A1 will be omitted.

In the cell determination device A1 according to the first embodiment of the present technology described above, the analysis unit 41 includes the calculation unit 411 and the determination unit 412. However, the cell determination device according to an embodiment of the present technology is not limited thereto. As in the cell determination device A2 according to the second embodiment, the classification unit 42 may have both of the function of calculating the physical properties and the function of classifying the cells based on the physical properties.

Figure 9:
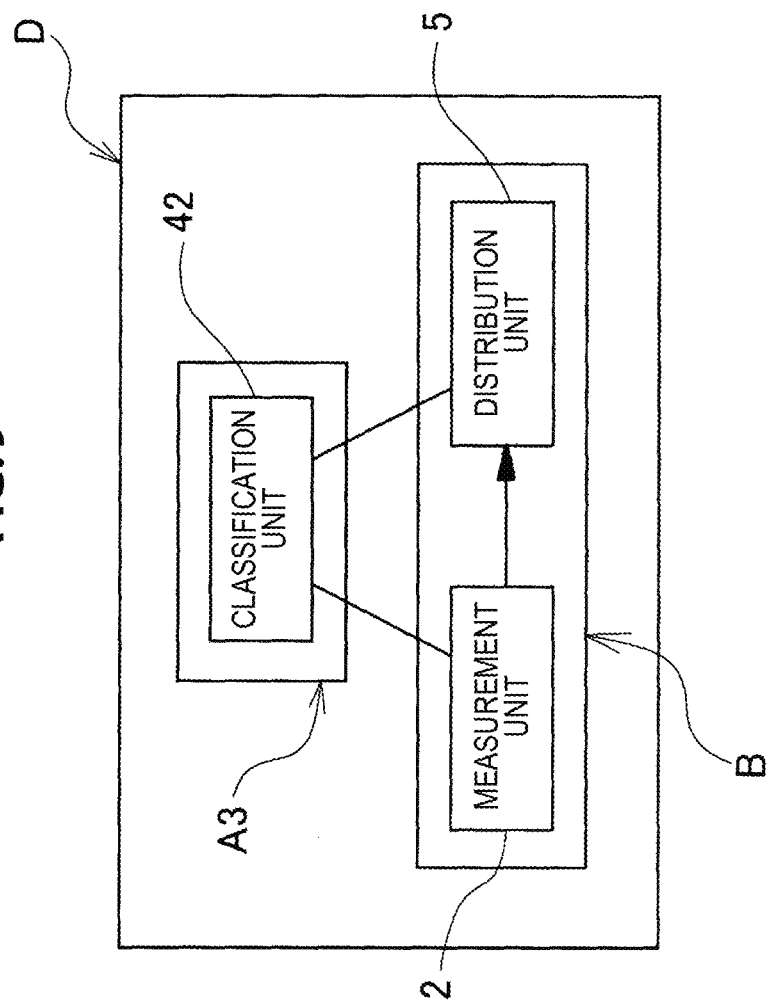
FIG. 9 is a block diagram illustrating the configuration of a cell determination system according to an embodiment of the present technology.

4. Cell Determination System According to an Embodiment of the Present Technology FIG. 9 is a block diagram illustrating a cell determination system according to an embodiment of the present technology. The cell determination system denoted by reference sign D in FIG. 9 includes a cell determination device A3 including a classification unit 42 that classifies cells based on physical properties obtained from a complex dielectric constant spectrum and a cell analysis device B including a measurement unit 2 that measures the complex dielectric constant spectrum. As in FIG. 1, an arrow illustrated in FIG. 9 indicates a direction in which a liquid (cell suspension) containing cells flows. The cell analysis device B may include a distribution unit 5 that divides cells into two or more groups based on a signal output by the classification unit 42. The configurations and the functions of the classification unit 42, the measurement unit 2, and the distribution unit 5 are the same as those of the cell determination devices A1 and A2 according to the first and second embodiments, and the description thereof will be omitted.

In the above-described cell determination devices A1 and A2, the measurement unit 2 and the distribution unit 5 is included in the cell determination devices A1 and A2. However, as in the cell determination system D, the measurement unit 2 and the distribution unit 5 may be configured as units separate from the cell determination device A3 in the cell determination device according to an embodiment of the present technology.

5. Specific Examples of Cells Classified by Cell Determination Device

The cell determination method according to an embodiment of the present technology described above will be described below exemplifying leukocytes, myocardial cells, and circulating tumor cells.

(1) Leukocytes

When the cells are leukocytes, the leukocytes are classified according to the kinds of leukocytes by the above-described cell determination method. The leukocytes are cells selected from lymphocytes, monocytes, neutrophils, acidocytes, and basocytes.

When the cells contained in the cell suspension are leukocytes selected from lymphocytes, monocytes, neutrophils, acidocytes, and basocytes, at least any one procedure of the following (i) to (iv) is preferably included in the above-described cell classification procedure S5 in order to divide the leukocytes into two groups:

(i) a procedure of dividing the leukocytes into two groups based on a predetermined value of the cell diameter d;

(ii) a procedure of dividing the leukocytes into two kinds of leukocytes based on a predetermined value of the relaxation strength De;

(iii) a procedure of dividing the leukocytes into two kinds of leukocytes based on a predetermined value of the film capacitance Cm; and (iv) a procedure of dividing the leukocytes into two groups based on a function that uses two or more variables selected from the physical properties.

By performing the procedure (i), five kinds of leukocytes can be divided into one group including lymphocytes or basocytes and another group including monocytes, neutrophils, or acidocytes based on the cell diameter d.

In the procedure (ii), the leukocytes can be divided into monocytes and neutrophils based on the relaxation strength De. In the procedure (iii), the leukocytes can be divided into lymphocytes and acidocytes based on the film capacitance Cm.

For the procedure (iv), for example, a function that uses the film capacitance Cm and the cytoplasm electric conductivity K as variables can be used. Based on this function, the leukocytes can be divided into lymphocytes and basocytes. Further, a function that uses the relaxation strength De and the relaxation frequency Fc as variables can be used. Based on this function, the leukocytes can be divided into two kinds of neutrophils and acidocytes or can be divided into two kinds of acidocytes and monocytes.

In the classification of the leukocytes performed according to the cell determination method according to an embodiment of the present technology, the cell suspension may not contain all of the five kinds of cells, lymphocytes, monocytes, neutrophils, acidocytes, and basocytes. Alternatively, the cell suspension may contain any two or more of the five kinds of cells of the leukocytes. For example, the cell suspension containing only some kinds of cells among the five kinds of leukocytes by performing density-gradient centrifugation in advance can also be used for the cell determination method according to an embodiment of the present technology.

When the cell suspension contains neutrophils, a procedure of determining a region including neutrophils as a criterion based on the cell diameter d and the film capacitance Cm may be included in the cell classification procedure S5. In this procedure S5, the cell diameter d and the film capacitance Cm of the measured neutrophils are first plotted in a two-dimensional scatter diagram form and the region of the neutrophils is determined from a distribution of the neutrophils. Next, boundaries for dividing the cells other than the neutrophils into a plurality of groups are determined from a predetermined value of the cell diameter d, a predetermined value of the film capacitance Cm, a function using the cell diameter d and the film capacitance Cm as variables, or the like which defines the region of the neutrophils. This procedure is suitable for, for example, classification of leukocytes including neutrophils.

The classification of neutrophils in the cell determination method according to an embodiment of the present technology can be applied not only to the classification of any of the foregoing five kinds of leukocytes but also to, for example, classification of lymphocytes as three kinds of T cells, B cells, and NK cells.

(2) Myocardial Cells

When the cells are cells other than myocardial cells, the cells are classified based on physical properties of the cells according to the above-described cell determination method. Particularly, the kinds of other cells are not limited. Examples of the cells include fibroblasts, blood cells, and endothelial cells.

When the cells contained in the cell suspension are cells of one or more selected from myocardial cells, fibroblasts, endothelial cells, and erythrocytes, at least any one procedure of the following (i) to (iii) is preferably included in the above-described cell classification procedure S5:

(i) a procedure of dividing the cells into two groups based on a predetermined value of the cell diameter d;

(ii) a procedure of dividing the cells into two kinds of cells based on a predetermined value of the film capacitance Cm; and (iii) a procedure of dividing the cells into two groups based on a function that uses two or more variables selected from the physical properties.

For example, by performing the foregoing procedure (i), the cells can be divided into one group including the myocardial cells and one group including the other cells based on the cell diameter d.

(3) Circulating Tumor Cells

When the cells are circulating tumor cells (CTC) and other cells, the cells are classified based on the physical properties of the cells according to the above-described cell determination method. A circulating tumor cell is defined as a tumor cell that circulates in a peripheral bloodstream of a cancer patient and is a tumor cell that permeates into a blood vessel from a primary tumor or a metastatic tumor. The detection of the circulating tumor cell is effective as early detection of metastatic malignancy. The detection of the circulating tumor cell is also important as a biomarker for predicting a state after the detection of the tumor or after treatment. The kinds of other cells described above are not particularly limited. For example, cells other than the circulating tumor cells contained in a peripheral blood, such as erythrocytes or leukocytes, are exemplified.

When the cells contained in the cell suspension are the circulating tumor cells and one or more cells selected from the cells contained in blood, at least any one procedure of the following (i) to (iii) is preferably included in the above-described cell classification procedure S5:

(i) a procedure of dividing the cells into two groups based on a predetermined value of the cell diameter d;

(ii) a procedure of dividing the cells into two groups based on a predetermined value of the relaxation frequency Fc; and (iii) a procedure of dividing the cells into two groups based on predetermined values of the cell diameter d and the relaxation frequency Fc.

For example, by performing any one of the foregoing procedures (i) to (iii), the cells can be classified as the circulating tumor cells based on the physical properties obtained from the complex dielectric constant spectrum of the cells.

In the cell determination method performed using the cell determination devices A1, A2, and A3 according to embodiments of the present technology, cells can be classified individually based on at least any one of the relaxation strength De, the relaxation frequency Fc, and the low-frequency conductance $G_{low}$ obtained from the complex dielectric constant spectrum. Thus, for example, it is not necessary to use a specific antibody with respect to an antigen developing from the surface of the circulating tumor cell, unlike a cell search system used to detect the circulating tumor cell. Accordingly, it is possible to detect the circulating tumor cell without performing the preprocessing on the cell, such as dyeing using an antigen. Therefore, it is easy to use the circulating tumor cells distributed after the division in subsequent analysis or cultivation. As in a tumor cell for which an antigen does not develop in the cell surface, a type of circulating tumor cell which does not react to an antigen can also be detected in the cell determination method according to an embodiment of the present technology.

As will be indicated in Example 6 to be described below, in the detection of the circulating tumor cells by the classification of the cells based on the complex dielectric constant spectrum, the circulating tumor cells can also be further classified based on a difference in the physical property in addition to the number of cells. By dividing the circulating tumor cells into two or more groups, for example, it is also possible to detect a change in the properties of the tumor cells through treatment or progression.

6. Cell Determination Method and Cell Determination Program According to an Embodiment of the Present Technology The cell determination method according to an embodiment of the present technology corresponds to an operation performed by the calculation unit 411 and the determination unit 412 included in the analysis unit 41 of the cell determination device A1 or the classification unit 42 of the cell determination device A2 or the cell determination system D described above. A cell determination program executing the operation is stored in the analysis unit 41 of the cell determination device A1 or the classification unit 42 of the cell determination device A2 or the cell determination system D.

The cell determination program according to an embodiment of the present technology is stored and retained in a hard disk and is read to a memory under the control of a CPU and an OS, so that a manipulation related to the above-described calculation and classification is performed. The cell determination program can also be recorded on a computer-readable recording medium. The recording medium is not particularly limited as long as the recording medium is a computer-readable recording medium. Specifically, for example, a disk-type recording medium such as a flexible disk or a CD-ROM is used. A tape-type recording medium such as a magnetic tape may also be used. Some of the processes can also be configured by hardware such as a digital signal processor (DSP), an application specific integrated circuit (ASIC), a programming logic device (PLD), or a field-programmable gate array (FPGA), so that the processes can be performed at a high speed in coordination with the foregoing program.

Additionally, the present technology may also be configured as below.

(1) A cell determination device including:
a classification unit configured to classify individual cells based on one of a relaxation strength, a relaxation frequency, and low-frequency conductance obtained from a complex dielectric constant spectrum of the cells.

(2) The cell determination device according to (1),
wherein the classification unit calculates any one or more of a cell diameter of the cells, film capacitance, and cytoplasm electric conductivity, based on one or more of the relaxation strength, the relaxation frequency, and the low-frequency conductance.

(3) The cell determination device according to (2),
wherein the cell diameter is calculated based on the low-frequency conductance.

(4) The cell determination device according to (2) or (3),
wherein the film capacitance is calculated based on the relaxation strength and the low-frequency conductance.

(5) The cell determination device according to any one of (2) to (4),
wherein the cytoplasm electric conductivity is calculated based on the relaxation strength, the relaxation frequency, and the low-frequency conductance.

(6) The cell determination device according to any one of (2) to (5),
wherein the cells include at least leukocytes.

(7) The cell determination device according to any one of (2) to (6),
wherein the cells include at least myocardial cells.

(8) The cell determination device according to any one of (2) to (7),
wherein the cells include at least circulation tumor cells.

(9) The cell determination device according to any one of (1) to (8), further including:
a measurement unit configured to measure the complex dielectric constant spectrum.

(10) The cell determination device according to any one of (1) to (9), further including:
a distribution unit configured to divide the cells into two or more groups based on a signal output by the classification unit.

EXAMPLES

Example 1

1. Classification (1) of Leukocytes Based on Predetermined Values of Physical Properties It was verified whether leukocytes could be classified based on the cell diameter d among the physical properties based on the complex dielectric constant spectrum.

[Material and Method]

Cell suspensions containing each of the lymphocytes, monocytes, neutrophils, acidocytes, and basocytes were prepared from whole human blood by separating each of the five kinds of cells, lymphocytes, monocytes, neutrophils, acidocytes, and basocytes. The cell suspensions were each diluted at a density of about $1\times10^5$ ml to about $1\times10^7$ ml suitable for measurement of the cell determination device. For each cell suspension, complex resistance was separately measured and the complex dielectric constant spectrum was obtained. The relaxation strength De was obtained from the obtained complex dielectric constant spectrum. From the complex dielectric constant spectrum, the cell diameter d was calculated using the above-described expression (3) and the film capacitance Cm was calculated using expression (4).

[Results]
(1) Lymphocytes and Neutrophils
FIG. 10A illustrates a distribution diagram of the lymphocytes and the neutrophils in regard to two kinds of physical properties. In FIG. 10A, the vertical axis represents the film capacitance Cm and the horizontal axis represents the cell diameter d. As illustrated in FIG. 10A, it was confirmed that the lymphocytes and the neutrophils were divided and distributed into two groups using the predetermined value (d=about 8 μm) of the cell diameter as a boundary. A ratio (%) of the cells included in each region when a region is divided into two regions using the predetermined value of the cell diameter d is shown in Table 1.

TABLE 1

|  | d > 8 | d < 8 |
| --- | --- | --- |
| Lymphocytes (%) | 5 | 95 |
| Neutrophils (%) | 95 | 5 |

As shown in Table 1, 95% of the lymphocytes were present in a region of d<8 and 95% of the neutrophils were present in a region of d>8.

(2) Lymphocytes and Acidocytes
FIG. 10B illustrates a distribution diagram of the lymphocytes and the acidocytes in regard to two kinds of physical properties. In FIG. 10B, the vertical axis represents the film capacitance Cm and the horizontal axis represents the cell diameter d. As illustrated in FIG. 10B, it was confirmed that the lymphocytes and the acidocytes were divided and distributed into two groups using the predetermined value (d=about 8 μm) of the cell diameter as a boundary. A ratio (%) of the cells included in each region when a region is divided into two regions using the predetermined value of the cell diameter d is shown in Table 2.

TABLE 2

|  | d > 8 | d < 8 |
| --- | --- | --- |
| Lymphocytes (%) | 5 | 95 |
| Acidocytes (%) | 97 | 3 |

As shown in Table 2, 95% of the lymphocytes were present in a region of d<8 and 97% of the acidocytes were present in a region of d>8.

(3) Lymphocytes and Monocytes
FIG. 11A illustrates a distribution diagram of the lymphocytes and the monocytes in two kinds of physical properties. In FIG. 11A, the vertical axis represents the film capacitance Cm and the horizontal axis represents the cell diameter d. As illustrated in FIG. 11A, it was confirmed that the lymphocytes and the monocytes were divided and distributed into two groups using the predetermined value (d=about 8.2 μm) of the cell diameter as a boundary. A ratio (%) of the cells included in each region when a region is divided into two regions using the predetermined value of the cell diameter d is shown in Table 3.

TABLE 3

|  | d > 8.2 | d < 8.2 |
| --- | --- | --- |
| Lymphocytes (%) | 3 | 97 |
| Monocytes (%) | 84 | 16 |

As shown in Table 3, 97% of the lymphocytes were present in a region of d<8.2 and 84% of the monocytes were present in a region of d>8.2.

(4) Neutrophils and Basocytes
FIG. 11B illustrates a distribution diagram of the neutrophils and the basocytes in regard to two kinds of physical properties. In FIG. 11B, the vertical axis represents the film capacitance Cm and the horizontal axis represents the cell diameter d. As illustrated in FIG. 11B, it was confirmed that the neutrophils and the basocytes were divided and distributed into two groups using the predetermined value (d=about 8 μm) of the cell diameter as a boundary. A ratio (%) of the cells included in each region when a region is divided into two regions using the predetermined value of the cell diameter d is shown in Table 4.

TABLE 4

|  | d > 8 | d < 8 |
| --- | --- | --- |
| Neutrophils (%) | 95 | 5 |
| Basocytes (%) | 5 | 95 |

As shown in Table 4, 95% of the neutrophils were present in a region of d>8 and 95% of the basocytes were present in a region of d<8.

(5) Basocytes and Acidocytes
FIG. 12A illustrates a distribution diagram of the basocytes and the acidocytes in two kinds of physical properties. In FIG. 12A, the vertical axis represents the film capacitance Cm and the horizontal axis represents the cell diameter d. As illustrated in FIG. 12A, it was confirmed that the basocytes and the acidocytes were divided and distributed into two groups using the predetermined value (d=about 8 μm) of the cell diameter as a boundary. A ratio (%) of the cells included in each region when a region is divided into two regions using the predetermined value of the cell diameter d is shown in Table 5.

TABLE 5

|  | d > 8 | d < 8 |
| --- | --- | --- |
| Basocytes (%) | 3 | 97 |
| Acidocytes (%) | 95 | 5 |

As shown in Table 5, 97% of the basocytes were present in a region of d<8 and 95% of the acidocytes were present in a region of d>8.

(6) Basocytes and Monocytes
FIG. 12B illustrates a distribution diagram of the basocytes and the monocytes in regard to two kinds of physical properties. In FIG. 12B, the vertical axis represents the film capacitance Cm and the horizontal axis represents the cell diameter d. As illustrated in FIG. 12B, it was confirmed that the basocytes and the monocytes were divided and distributed into two groups using the predetermined value (d=about 8.2 μm) of the cell diameter as a boundary. A ratio (%) of the cells included in each region when a region is divided into two regions using the predetermined value of the cell diameter d is shown in Table 6.

TABLE 6

|  | d > 8.2 | d < 8.2 |
| --- | --- | --- |
| Basocytes (%) | 2 | 98 |
| Monocytes (%) | 84 | 16 |

As shown in Table 6, 98% of the basocytes were present in a region of d<8.2 and 84% of the monocytes were present in a region of d>8.2.

As indicated in the present example, when the cells are divided into two groups based on the predetermined value of the cell diameter d calculated from the complex dielectric constant spectrum of the cells using expression (3), 80% or more of each cell was present in one region. From the result, it was confirmed that the leukocytes could be classified according to the kinds of leukocytes using the physical properties calculated from the complex dielectric constant spectrum.

Example 2

2. Classification (2) of Leukocytes Based on Predetermined Values of Physical Properties For the leukocytes, the classification of the cells based on the physical properties other than the cell diameter d was verified. In the complex dielectric constant spectrum of the cells, the relaxation strength De and the relaxation frequency Fc were calculated using the data obtained in Example 1. The film capacitance Cm was calculated using the above-described expression (4).

[Result]

(1) Neutrophils and Monocytes

FIG. 13A illustrates a distribution diagram of the neutrophils and the monocytes in regard to two kinds of physical properties. In FIG. 13A, the vertical axis represents the relaxation frequency Fc and the horizontal axis represents the relaxation strength De. As illustrated in FIG. 13A, it was confirmed that the neutrophils and the monocytes were divided and distributed into two groups using the predetermined value (De=850) of the relaxation strength as a boundary. A ratio (%) of the cells included in each region when a region is divided into two regions using the predetermined value of the relaxation strength De is shown in Table 7.

TABLE 7

|  | De > 850 | De < 850 |
| --- | --- | --- |
| Neutrophils (%) | 7 | 93 |
| Monocytes (%) | 68 | 32 |

As shown in Table 7, 93% of the neutrophils were present in a region of De<850 and 68% of the monocytes were present in a region of De>850.

(2) Lymphocytes and Acidocytes

FIG. 13B illustrates a distribution diagram of the lymphocytes and the acidocytes in regard to two kinds of physical properties. In FIG. 13B, the vertical axis represents the film capacitance Cm and the horizontal axis represents the cell diameter d. The lymphocytes and the acidocytes were classified into two groups using the predetermined value of the cell diameter d as the boundary in Example 1. However, as illustrated in FIG. 13B, it was confirmed that the lymphocytes and the acidocytes were divided and distributed into two groups even using the predetermined value (Cm=about 1.05E-1) of the film capacitance Cm as a boundary. A ratio (%) of the cells included in each region when a region is divided into two regions using the predetermined value of the film capacitance Cm is shown in Table 8.

TABLE 8

|  | Cm > 1.05E-1 | Cm < 1.05E-1 |
| --- | --- | --- |
| Lymphocytes (%) | 93 | 7 |
| Acidocytes (%) | 7 | 93 |

As shown in Table 8, 93% of the lymphocytes were present in a region of Cm>1.05E-1 and 93% of the acidocytes were present in a region of Cm>1.05E-1.

As indicated in the present example, when the cells are divided into two groups based on the predetermined values of the relaxation strength De obtained from the complex dielectric constant spectrum of the cells and the film capacitance Cm calculated from the complex dielectric constant spectrum using expression (4), 65% or more of the cells were present in one region. From the result, it was confirmed that the leukocytes could be classified according to the kinds of leukocytes using the physical properties calculated from the complex dielectric constant spectrum.

Example 3

3. Classification of Leukocytes Based on Function Using Two Kinds of Physical Properties as Variables For the leukocytes, i.e., a combination of the leukocytes not applied to the determination by the predetermined value of any physical property, the classification of the cells based on the function that uses two physical properties as variables was verified. In the complex dielectric constant spectrum of the cells, the relaxation strength De and the relaxation frequency Fc were calculated using the data obtained in Example 1. The film capacitance Cm was calculated using the above-described expression (4) and the cytoplasm electric conductivity K was calculated using expression (5).

[Results]

(1) Lymphocytes and Basocytes

Figure 14:
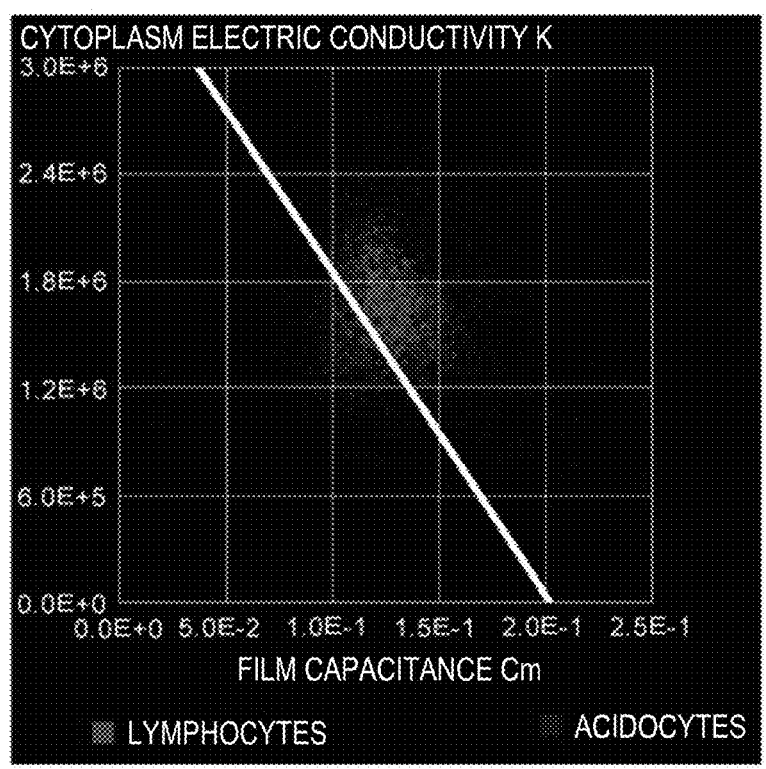
FIG. 14 is a diagram substitution graph illustrating distribution of leukocytes based on two kinds of physical properties.

FIG. 14 illustrates a distribution diagram of the lymphocytes and the basocytes in regard to two kinds of physical properties. In FIG. 14, the vertical axis (y axis) represents the cytoplasm electric conductivity K and the horizontal axis (x axis) represents the film capacitance Cm. As illustrated in FIG. 14, it was confirmed that the lymphocytes and the basocytes were divided and distributed into two groups using a function (y=ax+b, where a=−1.82E+7 and b=3.67E+6) indicated by a straight line in the drawing as a boundary. A ratio (%) of the cells included in each region when a region is divided into two regions using this function is shown in Table 9.

TABLE 9

|  | y > ax + b | y < ax + b |
| --- | --- | --- |
| Lymphocytes (%) | 89 | 11 |
| Basocytes (%) | 15 | 85 |

As shown in Table 9, when the region was divided using the foregoing function, 89% of the lymphocytes were present in a region of y>ax+b and 85% of the basocytes were present in a region of y<ax+b.

(2) Neutrophils and Acidocytes

Figure 15:
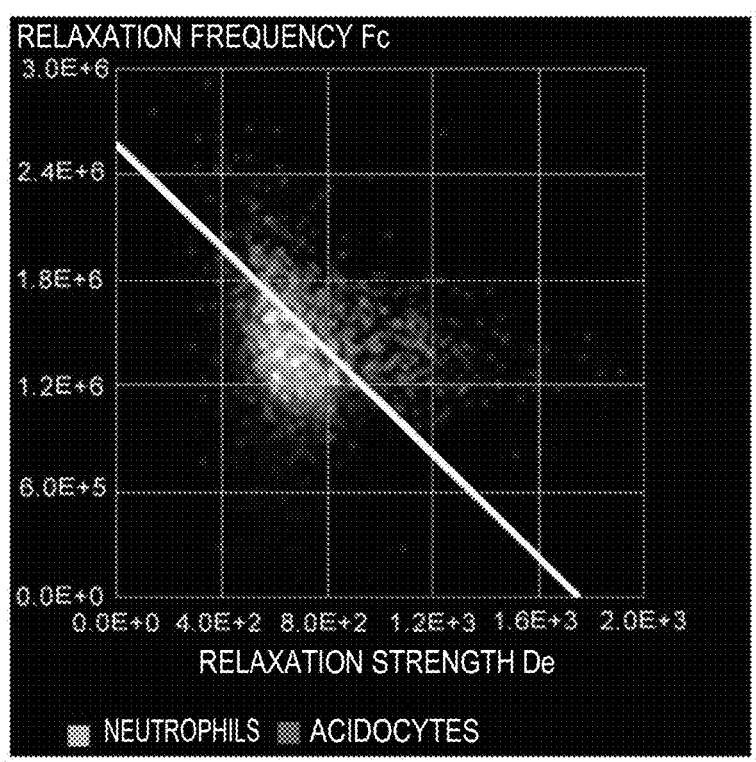
FIG. 15 is a diagram substitution graph illustrating distribution of leukocytes based on two kinds of physical properties.

FIG. 15 illustrates a distribution diagram of the neutrophils and the acidocytes in regard to two kinds of physical properties. In FIG. 15, the vertical axis (y axis) represents the relaxation frequency Fc and the horizontal axis (x axis)

represents the relaxation strength De. As illustrated in FIG. 15, it was confirmed that the neutrophils and the acidocytes were divided and distributed into two groups using a function (y=ax+b, where a=−1.47E+3 and b=2.58E+6) indicated by a straight line in the drawing as a boundary. A ratio (%) of the cells included in each region when a region is divided into two regions using this function is shown in Table 10.

TABLE 10

|  | y > ax + b | y < ax + b |
|---|---|---|
| Neutrophils (%) | 15 | 85 |
| Acidocytes (%) | 75 | 25 |

As shown in Table 10, when the region was divided using the foregoing function, 85% of the neutrophils were present in a region of y<ax+b and 75% of the acidocytes were present in a region of y>ax+b.

(3) Acidocytes and Monocytes

Figure 16:
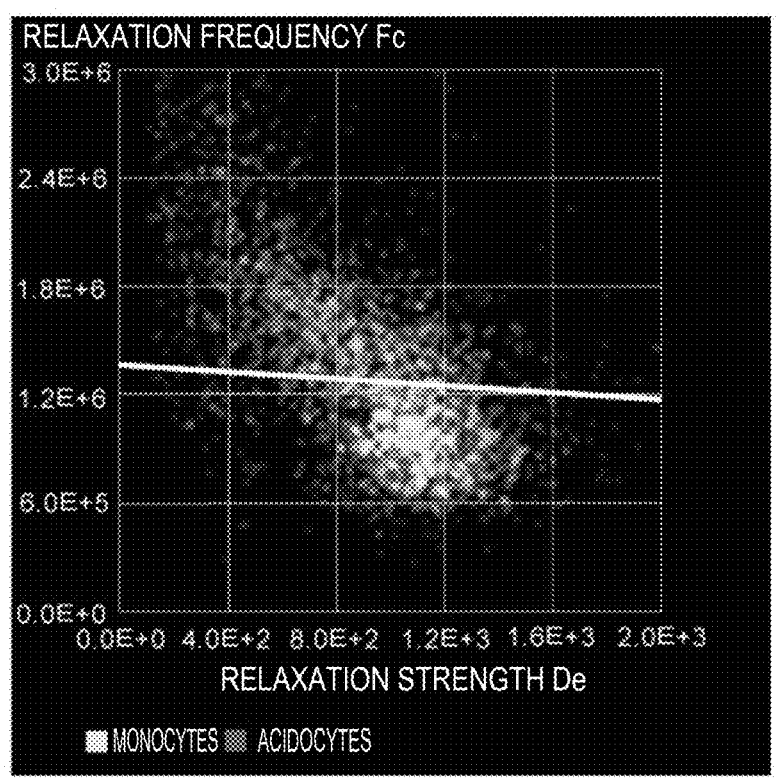
FIG. 16 is a diagram substitution graph illustrating distribution of leukocytes based on two kinds of physical properties.

FIG. 16 illustrates a distribution diagram of the acidocytes and the monocytes in regard to two kinds of physical properties. In FIG. 16, the vertical axis (y axis) represents the relaxation frequency Fc and the horizontal axis (x axis) represents the relaxation strength De. As illustrated in FIG. 16, it was confirmed that the acidocytes and the monocytes were divided and distributed into two groups using a function (y=ax+b, where a=−9.66E+1 and b=1.37E+6) indicated by a straight line in the drawing as a boundary. A ratio (%) of the cells included in each region when a region is divided into two regions using this function is shown in Table 11.

TABLE 11

|  | y > ax + b | y < ax + b |
|---|---|---|
| Acidocytes (%) | 85 | 15 |
| Monocytes (%) | 39 | 61 |

As shown in Table 11, when the region was divided using the foregoing function, 85% of the acidocytes were present in a region of y>ax+b and 61% of the monocytes were present in a region of y<ax+b.

From the results of the present example, when the cells are divided into two groups based on the function using the physical properties obtained from the complex dielectric constant spectrum of the cells as variables, it was confirmed that 60% or more of the cells were present in one region. From the result, it was indicated that the leukocytes could be classified according to the kinds of leukocytes using the function that uses the physical properties calculated from the complex dielectric constant spectrum as the variables.

Example 4

4. Classification of Cells Using Distribution of Neutrophils as Criterion

It was verified that leukocytes including neutrophils could be classified by using a distribution of the neutrophils based on the physical properties obtained from the complex dielectric constant spectrum as a criterion. In the complex dielectric constant spectrum of five kinds of leukocytes, the data obtained in Example 1 was used. From the complex dielectric constant spectrum, the cell diameter d was calculated using the above-described expression (3) and the film capacitance Cm was calculated using expression (4).

Figure 17:
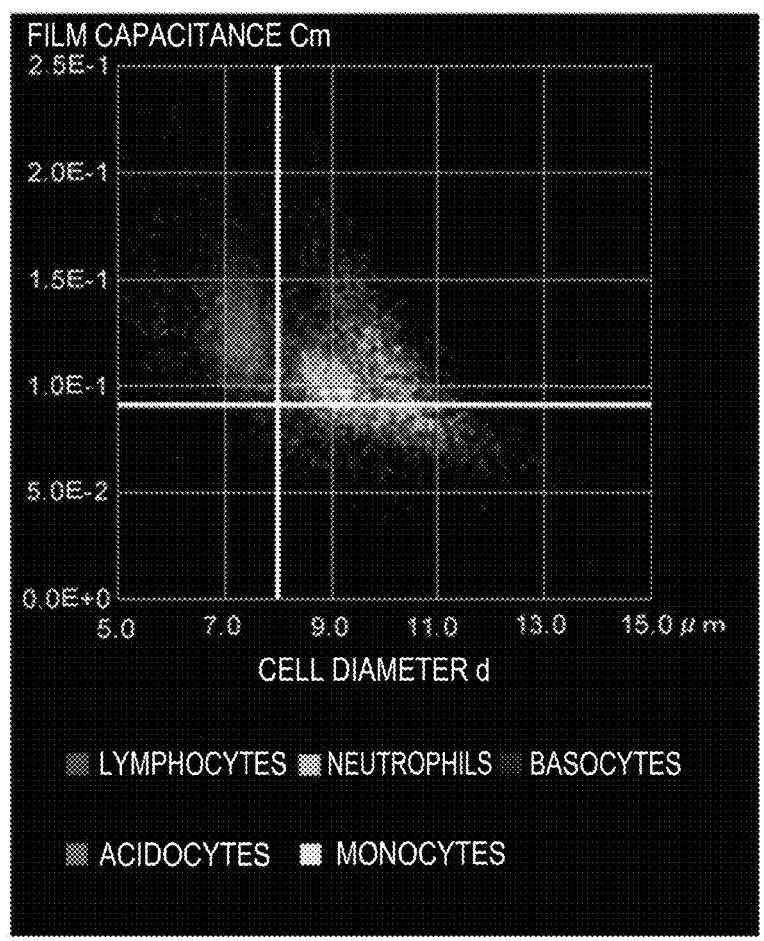
FIG. 17 is a diagram substitution graph illustrating a distribution of leukocytes based on a cell diameter and film capacitance.

FIG. 17 illustrates a distribution diagram of five kinds of leukocytes in regard to two kinds of physical properties. In FIG. 17, the vertical axis represents the film capacitance Cm and the horizontal axis represents the cell diameter d. Straight lines illustrated in FIG. 17 correspond to a lower limit (Cm=0.095) of the film capacitance Cm and a lower limit (d(µm)=8) of the cell diameter d of a portion defined as a region of the neutrophils based on the distribution of the neutrophils. A ratio (%) of the cells included in each group when the cells are divided into two groups using the lower limit is shown in Tables 12 and 13.

TABLE 12

|  | d > 8 | d < 8 |
|---|---|---|
| Neutrophils (%) | 93 | 7 |
| Basocytes (%) | 4 | 96 |
| Lymphocytes (%) | 7 | 93 |
| Acidocytes (%) | 97 | 3 |
| Monocytes (%) | 87 | 13 |

Table 12 shows a result obtained by dividing the cells into two groups based on the lower limit (d(µm)=8) of the cell diameter d of the region of the neutrophils. As shown in Table 12, the five kinds of leukocytes were present at ratios of 87% to 97% in any one region. From this result, the distribution of the cells of the leukocytes was shown to be biased when the lower limit of the cell diameter d of the region of the neutrophils was used as a boundary. Further, when the cells were divided into two groups using the lower limit of the cell diameter d of the region of the neutrophils, it was confirmed that the cells could be divided into two groups on the assumption that the neutrophils, the acidocytes, and the monocytes were one group and the basocytes and the lymphocytes were another group.

TABLE 13

|  | Cm > 0.095 | Cm < 0.095 |
|---|---|---|
| Neutrophils (%) | 91 | 9 |
| Basocytes (%) | 93 | 7 |
| Lymphocytes (%) | 97 | 3 |
| Acidocytes (%) | 25 | 75 |
| Monocytes (%) | 72 | 28 |

Table 13 shows a result obtained by dividing the cells into two groups based on the lower limit (Cm=0.095) of the film capacitance of the region of the neutrophils. As shown in Table 13, the five kinds of leukocytes were present at ratios of 72% to 97% in any one region. From this result, the distribution of the cells of the leukocytes was shown to be biased when the lower limit of the film capacitance Cm of the region of the neutrophils was a boundary. Further, when the cells were divided into two groups using the lower limit of the film capacitance of the region of the neutrophils, it was confirmed that the cells could be divided into two groups on the assumption that the neutrophils, the basocytes, the lymphocytes, and the monocytes were one group and the acidocytes were another group.

From the result of the present example, it was indicated that the leukocytes could be divided into two groups according the kinds of cells by using the region of the neutrophils based on the cell diameter d and the film capacitance Cm as the criterion.

Example 5

5. Classification of Cells Including Myocardial Based on Physical Properties It was verified whether cells including myocardial cells could be classified using the physical properties based on the complex dielectric constant spectrum.

[Material and Method]

For myocardial cells, a cell suspension suitable for measurement of complex resistance was prepared using commercially available rat myocardial cells. A cell suspension containing myocardial cells collected from a heart generally contains blood cells such as erythrocytes or cells other than myocardial cells, such as vascular endothelial cells or fibroblasts. Thus, for the cells contained in the cell suspension that contained the rat myocardial cells, the complex resistance was measured and permittivity was calculated from the complex resistance. Then, the cells contained in the cell suspension were classified based on the physical properties obtained from the complex dielectric constant spectrum of the cells. In the present example, the cell diameter d and the film capacitance Cm were used as the physical properties. From the complex dielectric constant spectrum, the cell diameter d was calculated using the above-described expression (3) and the film capacitance Cm was calculated using the above-described expression (4).

Apart from use for measurement, the cells contained in the cell suspension were also prepared for cultivation and the cells containing the myocardial cells were cultivated. A method of the related art was used as the cultivation method. On the first day after the cultivation, the cells were collected from a cultivation container through a trypinization process, the cells were prepared as a cell suspension, and the complex resistance of the cells contained in the cell suspension was measured.

A moving image for the cells of which the complex resistance was measured was captured using a camera so as to correspond to measurement data and the cells were classified as "spherical cells," "aspherical cells," "erythrocytes," and "others" collecting non-classifiable cells including cell debris according to the shapes of the captured cells. Based on the kinds of cells considered to be generally contained in the cell suspension used in the example, the "spherical cells" are estimated to be mainly myocardial cells and the "aspherical cells" are determined to be mainly fibroblasts.

[Results]

FIG. 18 illustrates a distribution diagram of the cells including the myocardial cells in regard to two kinds of physical properties. In FIGS. 18A and 18B, the vertical axis (y axis) represents the film capacitance Cm and the horizontal axis (x axis) represents the cell diameter d. FIG. 18A illustrates a distribution of the cells before start of the cultivation and FIG. 18B illustrates a distributions of the cells on the first day after the cultivation of the cells. The biased distributions of the cells are shown in the two-dimensional plots illustrated in FIGS. 18A and 18B based on the cell diameter d and the film capacitance Cm. Hereinafter, the results of the cells before the cultivation (see FIG. 18A) and the cells on the first day after the cultivation (see FIG. 18B) will be described in order.

[Result—Before Cultivation]

On the assumption that regions in which the cells are concentrated are set as regions 1 to 3 in the distribution of the cells illustrated in FIG. 18A, Table 14 shows the ranges of regions and ratios (%) of the spherical cells, the aspherical cells, the erythrocytes, and other cells included in the regions.

TABLE 14

| | Range Of Region | | Ratio Of Cells (%) | | | |
|---|---|---|---|---|---|---|
| Region | cell diameter (μm) | film capacitance | spherical cells | aspherical cells | eryth-rocytes | others |
| 1 | 8.5-11.5 | 0.020-0.030 | 73 | 19 | 2 | 6 |
| 2 | 8.0-12.0 | 0.011-0.016 | 13 | 70 | 9 | 8 |
| 3 | 5.0-7.50 | 0.040-0.060 | 13 | 0 | 53 | 33 |

As shown in Table 14, about 70% of the cells included in region 1 were the spherical cells (myocardial cells) and about 70% of the cells included in region 2 were the aspherical cells (fibroblasts). About 50% of the cells included in region 3 were erythrocytes. This result indicates that a bias occurs in the distribution according to the kinds of cells in the distribution of the cells based on the film capacitance Cm and the cell diameter d obtained from the complex dielectric constant spectrum.

Straight lines illustrated in FIG. 18A are a straight line indicating the cell diameter (x)=8 μm and a function (y=ax+b, a=−1.16E-3, and b=3.02E-2). As illustrated in FIG. 18A, for example, when a region in which the cells distribute is divided into two groups according to a predetermined value (8 μm) of the cell diameter d, regions 1 and 2 are included in one group and region 3 is included in the other group. When the region is divided into two groups according to a function based on the variables of the cell diameter d and the film capacitance Cm, regions 1 and 3 are included in one region and region 2 is included in the other region. A predetermined value of the film capacitance Cm can also be used as a boundary so that regions 1 and 2 are included in one region and region 3 is included in the other region. As shown in Table 14, the spherical cells (myocardial cells), the aspherical cells (fibroblasts), and the erythrocytes are present at a high density in regions 1 to 3. Therefore, the cells can be classified according to the kinds of cells by using the predetermined value of the cell diameter d or the film capacitance Cm or the function based on the variable of the cell diameter d and the film capacitance Cm.

[Result—First Day after Cultivation]

On the assumption that regions in which the cells are concentrated are set as regions 1 and 2 in the distribution of the cells illustrated in FIG. 18B, Table 15 shows the ranges of regions and ratios (%) of the spherical cells, the aspherical cells, the erythrocytes, and the other cells included in the regions.

TABLE 15

| | Range Of Region | | Ratio Of Cells (%) | | | |
|---|---|---|---|---|---|---|
| Region | cell diameter (μm) | film capacitance | spher-ical cells | aspher-ical cells | eryth-rocytes | others |
| 1 | 13.35-16.0 | 0.017-0.030 | 65.22 | 32.61 | 0 | 2.17 |
| 2 | 8.0-12.0 | 0.010-0.014 | 10.81 | 86.49 | 0 | 2.7 |

As shown in Table 15, about nearly 70% of the cells included in region 1 were the spherical cells (myocardial cells) and about 90% of the cells included in region 2 were the aspherical cells (fibroblasts). Even for the cultivated cells, this result indicates that a bias occurs in the distribution according to the kinds of cells in the distribution of the cells based on the film capacitance Cm and the cell diameter d obtained from the complex dielectric constant spectrum. The cells were less than before the cultivation of the cells in a region corresponding to region 3 of FIG. 18A in the distribution diagram of the cells on the first day after the cultivation illustrated in FIG. 18B because the blood cells such as erythrocytes not attached to a cultivation container were considered to be removed in the course of the cultivation of the cells.

Straight lines illustrated in FIG. 18B are a straight line indicating the cell diameter (x)=7 µm and a function (y=ax+b, a=−1.16E-3, and b=3.02E-2). As illustrated in FIG. 18B, for example, when the region is divided into two groups according to a function based on the variables of the cell diameter d and the film capacitance Cm, region 1 is included in one region and region 2 is included the other region. As shown in Table 15, the spherical cells (myocardial cells) and the aspherical cells (fibroblasts) are present at a high density in regions 1 and 2. Therefore, the cells can be classified according to the kinds of cells by using the function based on the variable of the cell diameter d and the film capacitance Cm.

The results of the present example indicate that the cells can be classified according to the kinds of cells based on the physical properties obtained from the complex dielectric constant spectrum of the cells including the myocardial cells. It was confirmed that the cells including the myocardial cells could be classified according to the kinds of cells based on the predetermined value of the cell diameter d or the predetermined value of the film capacitance Cm or the function using two kinds of physical properties as variables.

Example 6

6. Classification of Cells Including Cancer Cells Based on Physical Properties

It was verified whether cells including cancer cells could be classified using the physical properties based on the complex dielectric constant spectrum.

[Material and Method]

In the present example, HT29 cells and RKO cells derived from human colon cancer were used as the cancer cells. For the cancer cells, cell suspensions suitable for measurement of the complex resistance were prepared. A process of removing most of the leukocytes and erythrocytes from blood of a non-cancer patient using density-gradient centrifugation and magnetic beads in which an anti-CD 45 antibody or an anti-CD 235A antibody was combined was performed to obtain processed blood. In the present example, the processed blood is referred to as normal blood sample. A cell suspension suitable for the measurement of the complex resistance was prepared for the normal blood sample as well.

The complex resistance of the cells contained in each of the foregoing three kinds of cell suspensions was measured to obtain the complex dielectric constant spectrum. Based on the physical properties obtained from the complex dielectric constant spectrum, a distribution of the cells contained in each of the cell suspensions was inspected. In the example, the relaxation frequency Fc, the cell diameter d, and the cytoplasm electric conductivity K were used as the physical properties. From the complex dielectric constant spectrum, the cell diameter d was calculated using the above-described expression (3) and the cytoplasm electric conductivity K was calculated using the above-described expression (5).

[Results]

Figure 20:
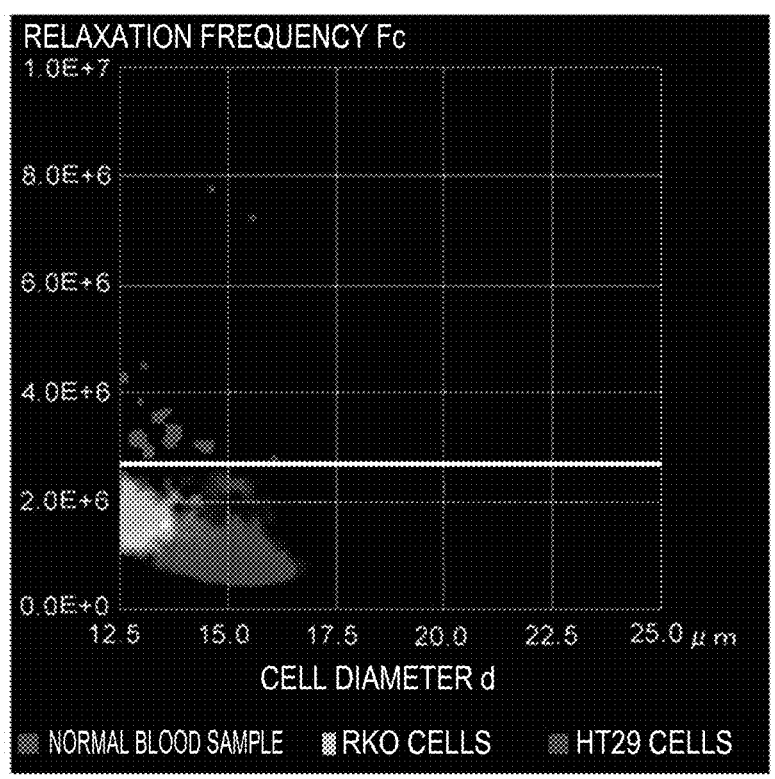
FIG. 20 is a diagram substitution graph expanding a part.
Figure 21:
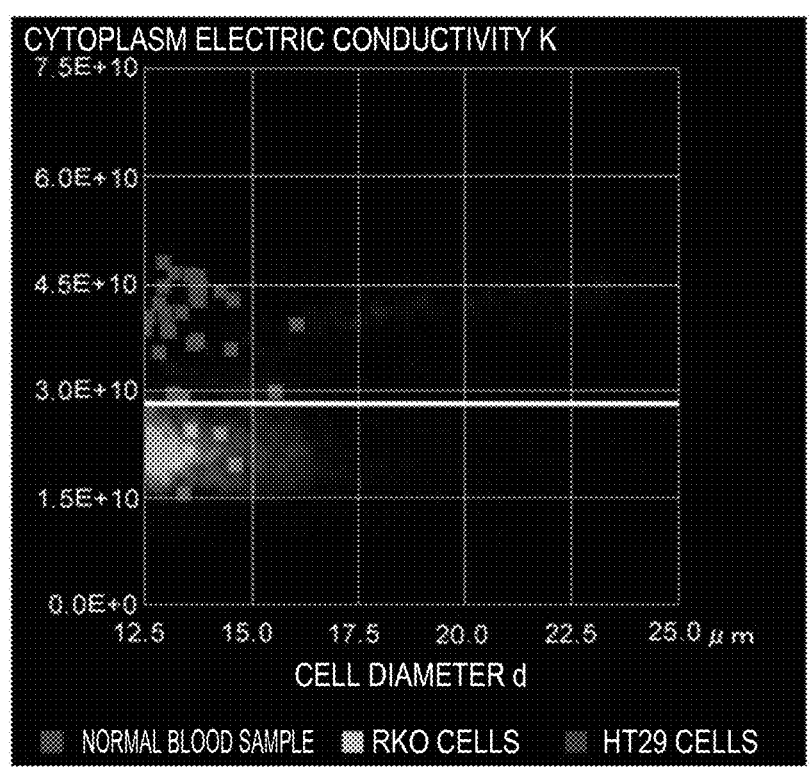
FIG. 21 is a diagram substitution graph illustrating distributions of a normal blood sample, H29 cells, and RKO cells based on a cell diameter and cytoplasm electric conductivity.

FIGS. 19 to 21 illustrate the results of the present example. In FIGS. 19 to 20, the vertical axis (y axis) represents the relaxation frequency Fc and the horizontal axis (x axis) represents the cell diameter d. In FIG. 21, the vertical axis (y axis) represents the cytoplasm electric conductivity K and the horizontal axis (x axis) represents the cell diameter d. FIG. 19A illustrates a distribution diagram of the cells contained in the foregoing normal blood sample in regard to the cell diameter d and the relaxation frequency Fc and FIG. 19B illustrates a distribution diagram of the HT29 cells and the RKO cells in regard to the cell diameter d and the relaxation frequency Fc. In FIG. 20, the distributions of the cells illustrated in FIGS. 19A and 19B are superimposed, and then a range in which the cell diameter d exceeds 12.5 µm is expanded.

As illustrated in FIG. 19A, the cells contained in the normal blood sample were concentrated in a region in which the cell diameter d was equal to or less than 12.5 µm. On the other hand, as illustrated in FIGS. 19B and 20, the HT29 cells and the RKO cells were concentrated in a region in which the relaxation frequency Fc was less than 2.5 MHz (a straight line illustrated in FIG. 20 indicates the relaxation frequency Fc=2.5 MHz). Even when the HT29 cells and the RKO cells were the same cells derived from colon cancer, there was a difference in the distribution in regard to the cell diameter d. FIG. 21 illustrates a distribution diagram of the HT29 cells, the RKO cells, and the cells derived from the normal blood sample in regard to the cell diameter d and the cytoplasm electric conductivity K. As illustrated in FIG. 21, when the region was delimited based on the cytoplasm electric conductivity K, the HT29 cells and the RKO cells were concentrated in a region in which the cytoplasm electric conductivity K was less than 2.8E10 (a straight line illustrated in FIG. 21 indicates the cytoplasm electric conductivity K=2.8E10).

From the foregoing results, a bias was recognized in the distributions of the cancer cells and the cells contained in the blood based on the cell diameter d, and the relaxation frequency Fc or the cytoplasm electric conductivity K obtained from the complex dielectric constant spectrum. Accordingly, it was indicated that the cells could be classified as the cancer cells and the other cells based on the cell diameter d, and the relaxation frequency Fc or the cytoplasm electric conductivity K. For the HT29 cells and the RKO cells, from the recognition of the difference in the distribution in regard to the cell diameter d, it was indicated that the cancer cells could be classified more precisely based on the physical properties obtained from the complex dielectric constant spectrum.

Example 7

7. Classification of Cells Including Circulating Tumor Cells Based on Physical Properties In Example 6, it was indicated that the cells could be classified as the cancer cells and the other cells based on the physical properties obtained from the complex dielectric constant spectrum. In the present example, it was verified that the classification could be applied to the circulating tumor cells.

[Material and Method]

In the present example, a sample in which the foregoing cells derived from a colon cancer were mixed in the normal blood sample of Example 6 was prepared instead of blood containing the circulating tumor cells. In the present example, this sample is referred to as a tumor cell mixture blood sample. The tumor cell mixture blood sample was prepared as a cell suspension suitable for measurement of the complex resistance. The complex resistance of the cells contained in the cell suspension was measured to obtain the complex dielectric constant spectrum. The cells were classified based on the physical properties obtained from the complex dielectric constant spectrum. In the example, the relaxation frequency Fc and the cell diameter d were used as the physical properties. From the complex dielectric constant spectrum, the cell diameter d was calculated using the above-described expression (3).

[Results]

Figure 22:
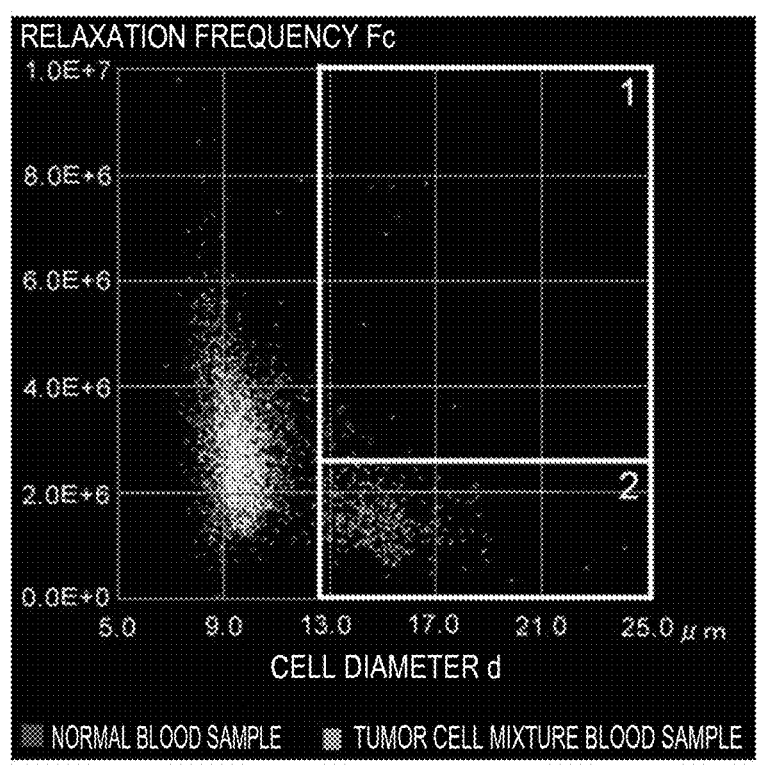
FIG. 22 is a diagram substitution graph illustrating distributions of cells contained in a normal blood sample and cells contained in a tumor cell mixture blood sample based on a cell diameter and a relaxation frequency.

FIG. 22 illustrates the results of the present example. In FIG. 22, the vertical axis (y axis) represents the relaxation frequency Fc and the horizontal axis (x axis) represents the cell diameter d. FIG. 22 illustrates the superimposed distributions of the cells contained in the normal blood sample and the cells contained in the tumor cell mixture blood sample in regard to the cell diameter d and the relaxation frequency Fc. In FIG. 22, region 1 is a region in which the cell diameter d exceeds 12.5 μm and region 2 is a region in which the cell diameter d exceeds 12.5 μm and the relaxation frequency Fc is less than 2.5 MHz. Table 16 shows the numbers of cells (units) present in each of regions 1 and 2. The number of cells contained in the normal blood sample and the number of cells contained in the tumor cell mixture blood sample illustrated in FIG. 22 are 1475 and 2019, respectively.

TABLE 16

| | Range Of Region | | Number Of Cells | |
|---|---|---|---|---|
| Region | cell diameter (μm) | relaxation frequency (MHz) | normal blood sample | tumor cell mixture blood sample |
| 1 | x > 12.5 | — | 29 | 350 |
| 2 | x > 12.5 | y < 2.5 | 3 | 333 |

As shown in Table 16, of the cells contained in the tumor cell mixture blood sample, 350 cells were present in region 1 and 333 cells were present in region 2. On the other hand, of the cells contained in the normal blood sample, 29 cells were present in region 1 and 3 cells were present in region 2. The normal blood sample contains no tumor cells (HT20 cells or RKO cells). Therefore, the number of cells which are the cells present in each region and are the cells contained in the normal blood sample indicates accurate determination when the cells included in the region are determined as tumor cells.

As shown in Table 16, while the number of cells contained in the normal blood sample was about 2% of the total number, the number of cells contained in the tumor cell mixture blood sample was about 17% of the total number. Accordingly, even when the HT29 cells and the RKO cells were mixed in the normal blood sample, it was confirmed that the cells could be classified as the tumor cells and the other cells based on the cell diameter d obtained from the complex dielectric constant spectrum. That is, it was indicated that the circulating tumor cells could be classified according to the cell determination method according to an embodiment of the present technology.

In region 2 based on the relaxation frequency Fc in addition to the cell diameter d, the number of cells contained in the normal blood sample was reduced to about 1/10 that of region 1. This indicates that in the classification of the circulating tumor cells, the classification of the cells other than the tumor cells as the tumor cells is further decreased by using the cell diameter d and the relaxation frequency Fc. From the foregoing result, when the circulating tumor cells are classified according to the cell determination method according to an embodiment of the present technology, it is preferable to use two or more physical properties and it is preferable to combine the cell diameter d and the relaxation frequency Fc.

INDUSTRIAL APPLICABILITY

According to the cell determination method according to an embodiment of the present technology, the cells can be classified without processing the cells with a reagent such as stain, and thus it is possible to reduce the influence of the reagent on the cells. Therefore, the cell determination method according to an embodiment of the present technology can be used for a therapy method of cultivating self-cells and returning only specific kinds of cells again into a body or regenerative medicine of selecting and using cells specialized from cultivated cells to target cells.

REFERENCE SIGNS LIST

A1, A2, A3 cell determination device
B cell analysis device
C, C1, C2 cell
D cell determination system
1 preprocessing unit
2 measurement unit
21 flow passage
22 cover layer
23a, 23b flow passage layer
24 intermediate layer
25a, 25b electrode
26 stricture portion
3 detection unit
41 analysis unit
42 classification unit
411 calculation unit
412 determination unit
5 distribution unit
51 electric field application unit
511a, 511b electrode
512 flow passage
52, 52a, 52b branch flow passage

The invention claimed is:

1. A cell determination device, comprising:
a memory configured to store instructions; and
a circuitry configured to execute the instructions stored in the memory to:
obtain a relaxation strength and a low frequency conductance from a complex dielectric constant spectrum of cells; and
calculate a film capacitance of the cells based on the relaxation strength;
calculate a cell diameter of the cells based on the low-frequency conductance and two parameters that depend on a configuration of a flow passage of a measurement unit configured to measure the complex dielectric constant spectrum of the cells, wherein the cell diameter is calculated based on a first relaxation expression:

$d=(G_{low}/a)^{1/b}$, wherein $G_{low}$ indicates the low-frequency conductance, and a and b indicate the two parameters, and wherein each of the two parameters is an integer; and classify the cells based on the film capacitance and the cell diameter.

2. The cell determination device according to claim 1, wherein the circuitry is further configured to:
obtain a relaxation frequency from the complex dielectric constant spectrum of the cells; and
calculate a cytoplasm electric conductivity, based on at least one of the relaxation strength, the relaxation frequency, or the low-frequency conductance.

3. The cell determination device according to claim 2, wherein the circuitry is further configured to calculate the cytoplasm electric conductivity based on the relaxation strength, the relaxation frequency, and the low-frequency conductance.

4. The cell determination device according to claim 1, wherein the circuitry is further configured to calculate the film capacitance based on the relaxation strength and the low-frequency conductance.

5. The cell determination device according to claim 1, wherein the cells include at least leukocytes.

6. The cell determination device according to claim 1, wherein the cells include at least myocardial cells.

7. The cell determination device according to claim 1, wherein the cells include at least circulation tumor cells.

8. The cell determination device according to claim 1, further comprising a flow cytometer configured to divide the cells into a plurality of groups based on a signal output by the circuitry.

9. The cell determination device according to claim 1, wherein the circuitry is further configured to classify each cell in to at least one group based on at least one of the cell diameter of the cells, the film capacitance, or a cytoplasm electric conductivity.

10. The cell determination device according to claim 1, wherein the low-frequency conductance is an electric conductivity of the cells obtained from the complex dielectric constant spectrum of cells at a frequency equal to or less than 500 kHz.

11. The cell determination device according to claim 1, wherein the film capacitance is calculated based on a second relaxation expression:

$C_m = D_e/d^1$, wherein $D_e$ indicates the relaxation strength and d indicates the cell diameter of the cells.

12. A cell determination system, comprising:
a cell analysis device including a circuitry configured to measure a complex dielectric constant spectrum of cells; and
a cell determination device configured to:
obtain a relaxation strength and a low-frequency conductance from the complex dielectric constant spectrum of the cells;
calculate a film capacitance of the cells based of the relaxation strength;
calculate a cell diameter of the cells based on the low-frequency conductance and two parameters that depend on a configuration of a flow passage of a measurement unit configured to measure the complex dielectric constant spectrum of the cells, wherein the cell diameter is calculated based on a relaxation expression:

$d=(G_{low}/a)^{1/b}$, wherein $G_{low}$ indicates the low-frequency conductance, and a and b indicate the two parameters, and wherein each of the two parameters is an integer; and classify the cells based on the film capacitance and the cell diameter.

13. The cell determination system according to claim 12, wherein the cell analysis device further includes a flow cytometer configured to divide the cells into a plurality of groups based on a signal output by the cell determination device.

14. A cell determination method, comprising:
measuring a complex dielectric constant spectrum of cells;
determining a relaxation strength and a low-frequency conductance based on the complex dielectric constant spectrum of the cells;
calculating a film capacitance of the cells based on the relaxation strength;
calculating a cell diameter of the cells based on the low-frequency conductance and two parameters that depend on a configuration of a flow passage of a measurement unit configured to measure the complex dielectric constant spectrum of the cells, wherein the cell diameter is calculated based on a relaxation expression:

$d=(G_{low}/a)^{1/b}$, wherein $G_{low}$ indicates the low-frequency conductance, and a and b indicate the two parameters, and wherein each of the two parameters is an integer; and classifying the cells based on the film capacitance and the cell diameter.

15. A non-transitory computer-readable storage medium having stored thereon, computer-executable instructions for causing a computer to execute operations, the operations comprising:
measuring a complex dielectric constant spectrum of cells;
determining a relaxation strength and a low-frequency conductance based on the complex dielectric constant spectrum of the cells;
calculating a film capacitance of the cells based on the relaxation strength;
calculating a cell diameter of the cells based on the low-frequency conductance and two parameters that depend on a configuration of a flow passage of a measurement unit configured to measure the complex dielectric constant spectrum of the cells, wherein the cell diameter is calculated based on a first relaxation expression:

$d=(G_{low}/a)^{1/b}$, wherein $G_{low}$ indicates the low-frequency conductance, and a and b indicate the two parameters, and wherein each of the two parameters is an integer; and classifying the cells based on the film capacitance and the cell diameter.

* * * * *